US006626885B2

(12) United States Patent
Massengale

(10) Patent No.: US 6,626,885 B2
(45) Date of Patent: Sep. 30, 2003

(54) METHOD OF FLUID DELIVERY AND CATHETERS FOR USE WITH SAME

(75) Inventor: Roger Dillard Massengale, Mission Viejo, CA (US)

(73) Assignee: I-Flow Corporation, Lake Forest, CA (US)

(*) Notice: Subject to any disclaimer, the term of this patent is extended or adjusted under 35 U.S.C. 154(b) by 0 days.

(21) Appl. No.: 09/815,888

(22) Filed: Mar. 23, 2001

(65) Prior Publication Data
US 2002/0052576 A1 May 2, 2002

Related U.S. Application Data

(63) Continuation-in-part of application No. PCT/US00/19746, filed on Jul. 18, 2000, which is a continuation-in-part of application No. 09/363,228, filed on Jul. 19, 1999.

(51) Int. Cl.7 .............................................. A61M 31/00
(52) U.S. Cl. ....................................................... 604/508
(58) Field of Search .......................... 604/28, 500, 506, 604/507, 508, 510, 511, 512, 93.01, 164.01, 171, 264; 128/898

(56) References Cited

U.S. PATENT DOCUMENTS

| 3,595,241 A | 7/1971 | Sheridan |
| 3,821,956 A | 7/1974 | Gordhamer |
| 4,412,832 A * | 11/1983 | Kling et al. ................ 604/161 |
| 5,066,278 A | 11/1991 | Hirschberg et al. |
| 5,184,627 A | 2/1993 | De Toledo |
| 5,201,723 A | 4/1993 | Quinn |
| 5,267,979 A | 12/1993 | Appling et al. |
| 5,269,755 A | 12/1993 | Bodicky |
| 5,356,388 A | 10/1994 | Sepetka et al. |
| 5,376,083 A | 12/1994 | Mische |
| 5,425,723 A | 6/1995 | Wang |
| 5,643,228 A | 7/1997 | Schucart et al. |
| 5,702,372 A | 12/1997 | Nelson |
| 5,709,874 A | 1/1998 | Hanson et al. |
| 5,776,111 A | 7/1998 | Tesio |
| 5,800,407 A | 9/1998 | Eldor |
| 5,833,652 A | 11/1998 | Preissman et al. |
| 5,846,216 A | 12/1998 | Gonzales et al. |
| 5,919,160 A * | 7/1999 | Sanfilippo, II ................ 604/19 |
| 5,968,017 A * | 10/1999 | Lampropoulos et al. .... 604/154 |
| 6,179,816 B1 * | 1/2001 | Mottola et al. ................ 315/39 |
| 6,368,315 B1 * | 4/2002 | Gillis et al. .................. 604/523 |

FOREIGN PATENT DOCUMENTS

| DE | 3400874 C1 | 1/1984 |
| EP | 0 804 936 A2 | 11/1997 |
| FR | 2 539 298 | 1/1983 |
| FR | 2 622 805 | 11/1987 |
| GB | 2 277 035 | 10/1994 |
| JP | 4-327857 | 11/1992 |
| WO | WO 92/00113 | 1/1992 |
| WO | WO 92/11895 | 7/1992 |
| WO | WO 96/33761 | 10/1996 |
| WO | WO 7/49447 | 12/1997 |

* cited by examiner

Primary Examiner—Brian L. Casler
Assistant Examiner—Mark K. Han
(74) Attorney, Agent, or Firm—Knobbe Martens Olson & Bear LLP

(57) ABSTRACT

A pain management system for the infusion of drug to a wound site includes a guide needle placed within an introducer tubing. The needle and tubing are pierced through the patient's skin, after which the guide needle is withdrawn The infusion catheter is threaded through the introducer tubing and advanced to the wound site. The introducer tubing is withdrawn and preferably peeled off of the infusion catheter. In accordance with one embodiment, the catheter comprises an elongated tube with a plurality of exit holes along an infusion section of the catheter, and an elongated flexible porous member residing within the tube and forming an annular space between the tube and the member. In accordance with other embodiments, the catheter includes a plurality of exit holes, which combine to form a flow-restricting orifice of the catheter.

11 Claims, 11 Drawing Sheets

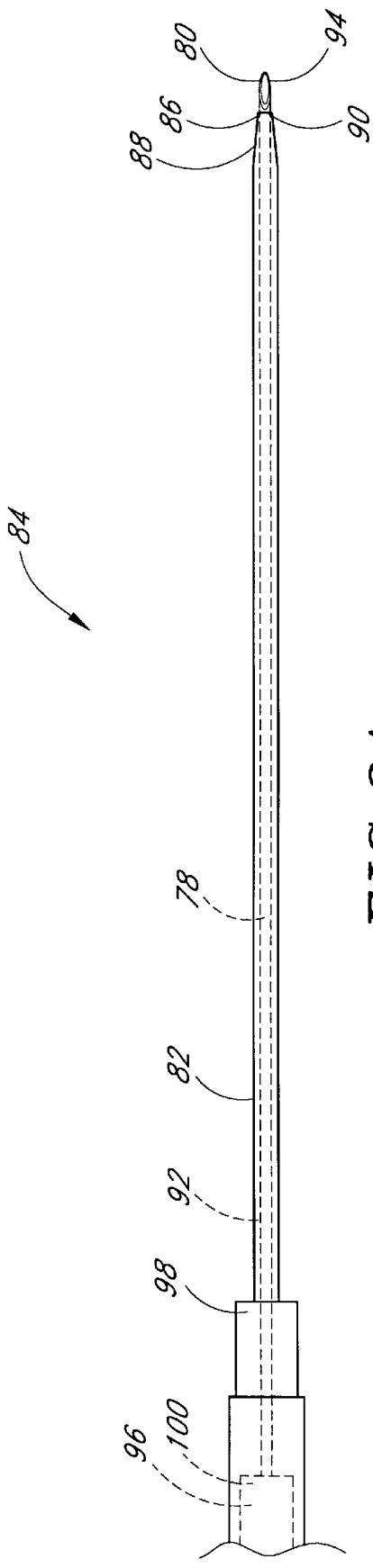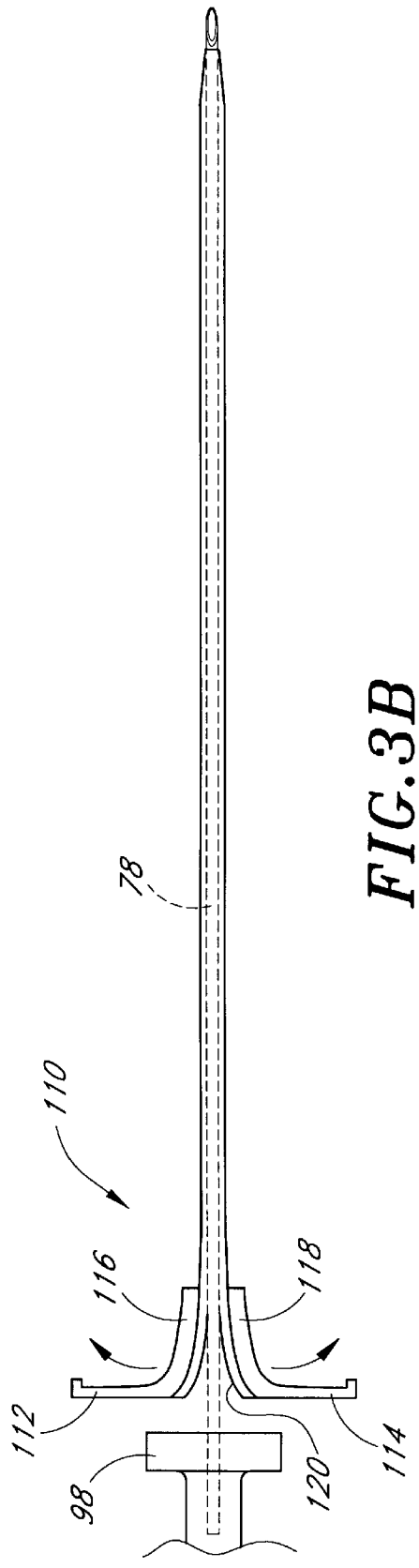

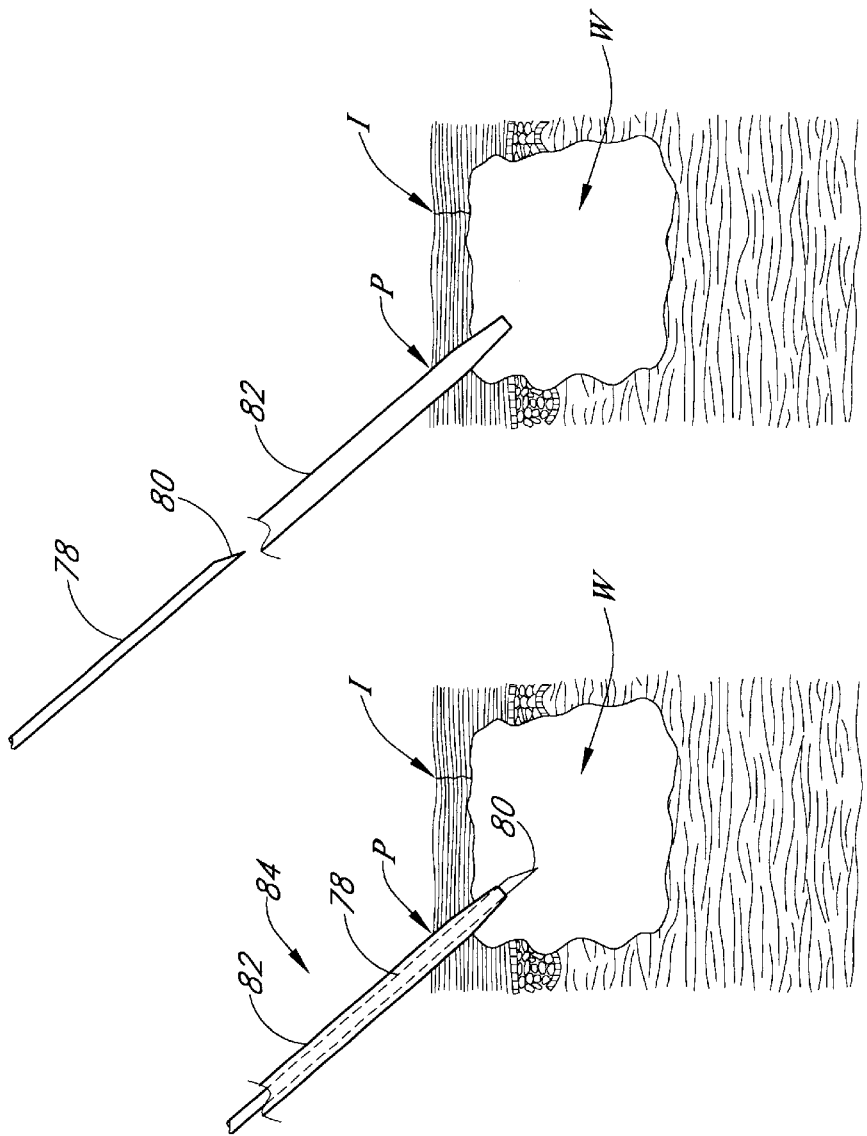
FIG. 6
FIG. 5
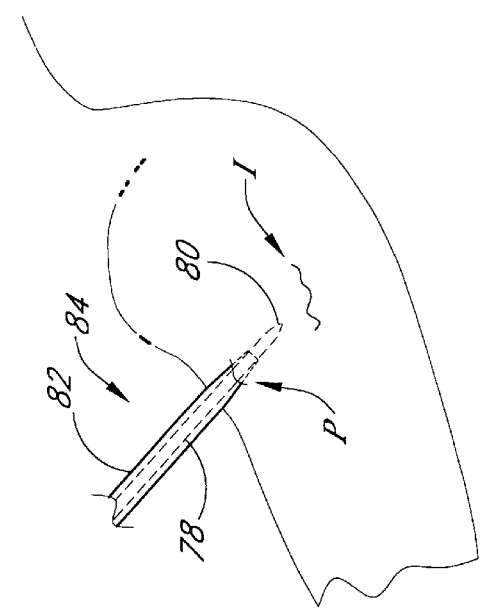
FIG. 4

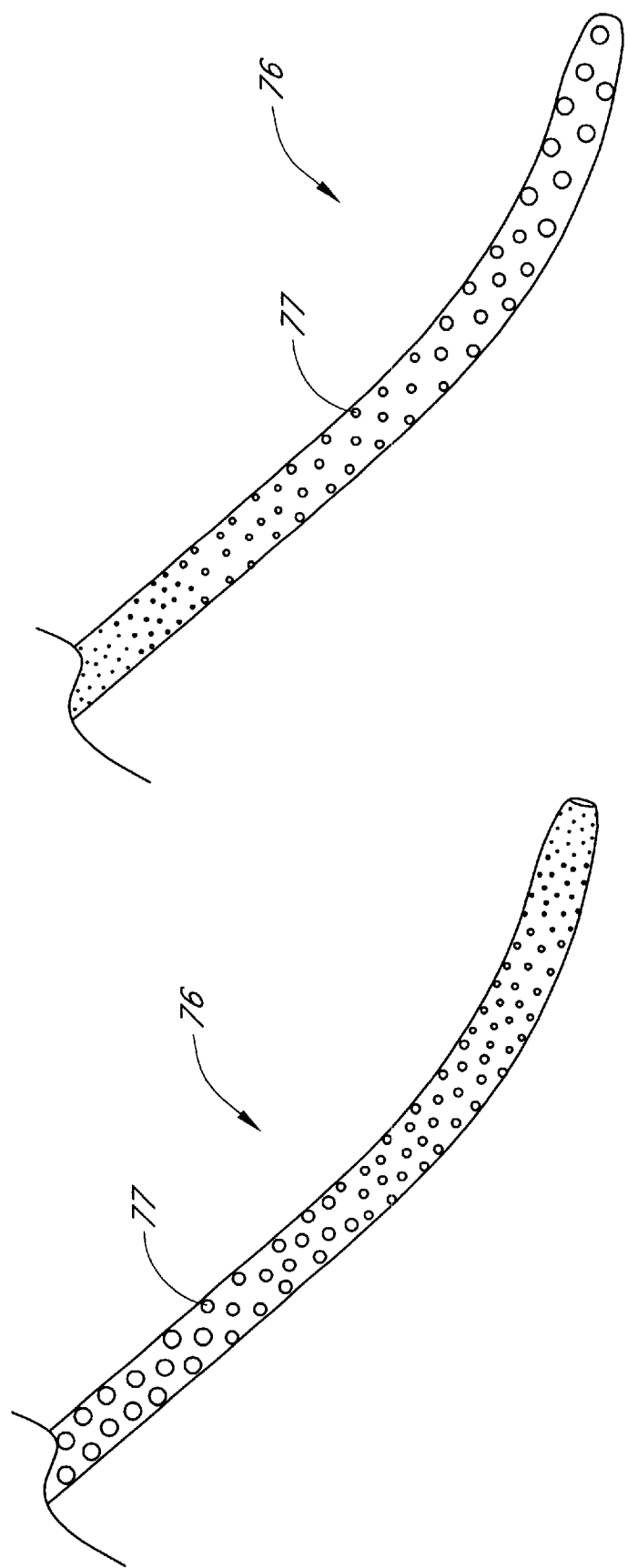

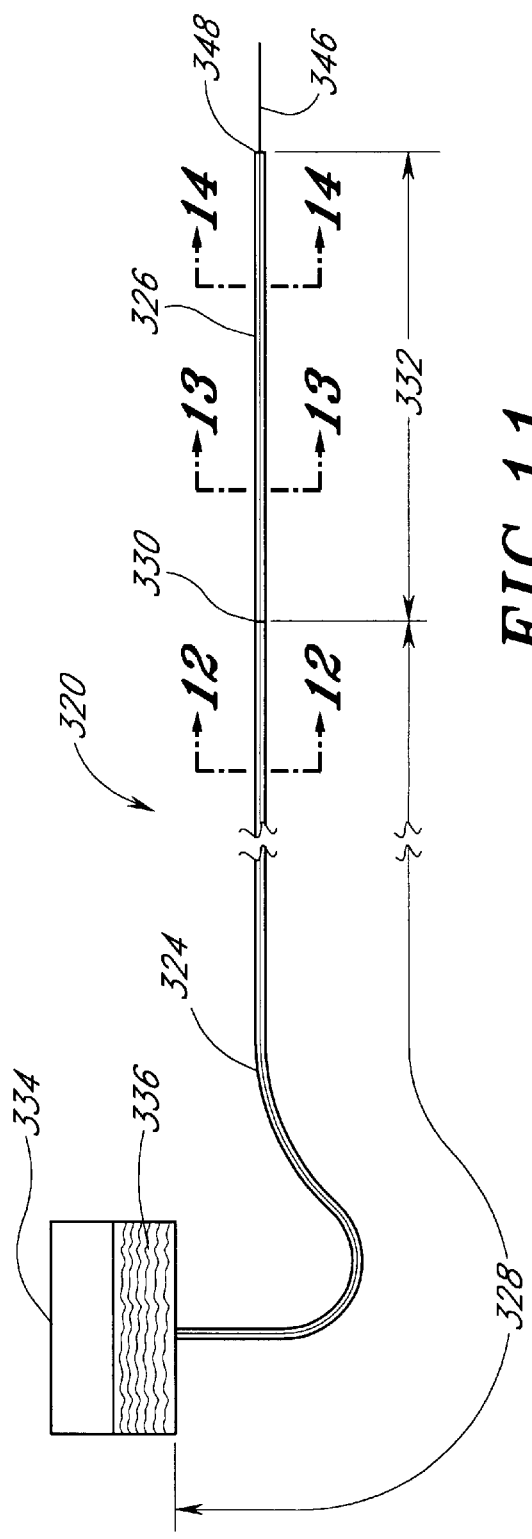
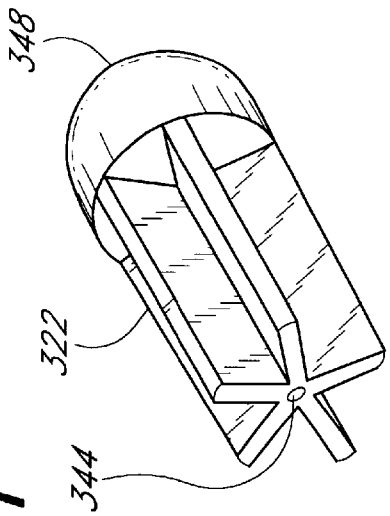
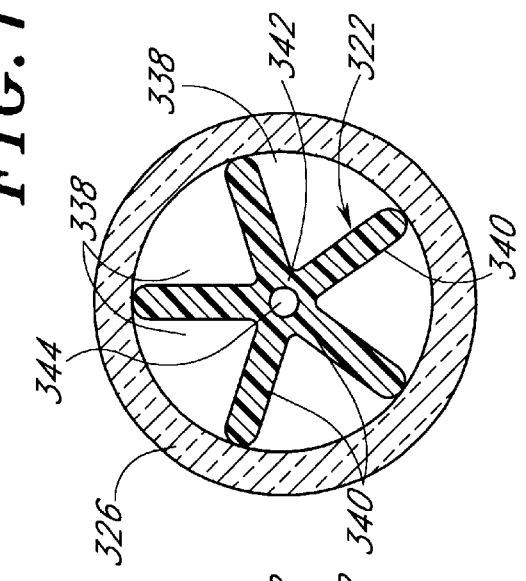
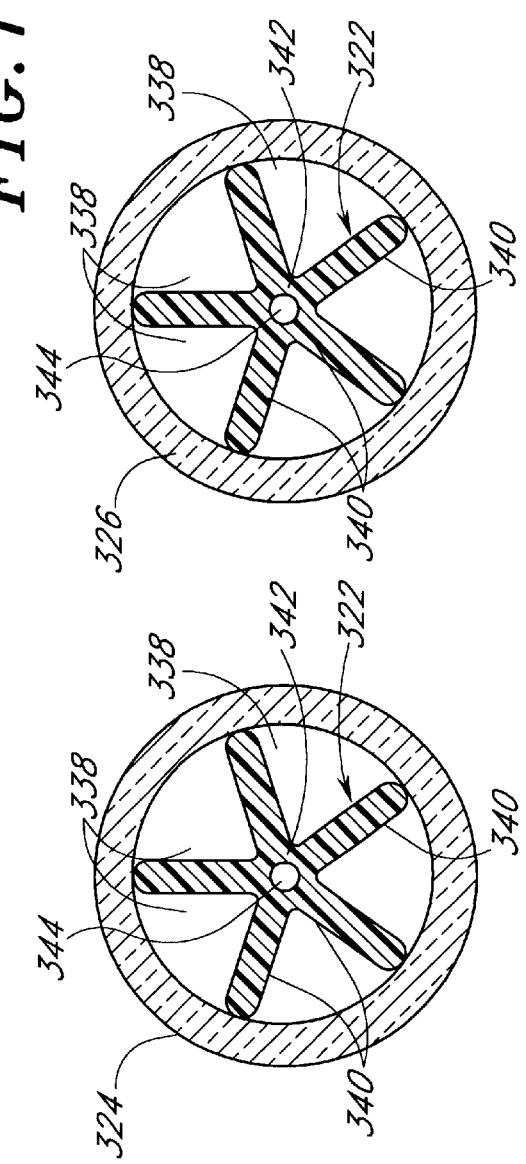
FIG. 11
FIG. 14
FIG. 13
FIG. 12

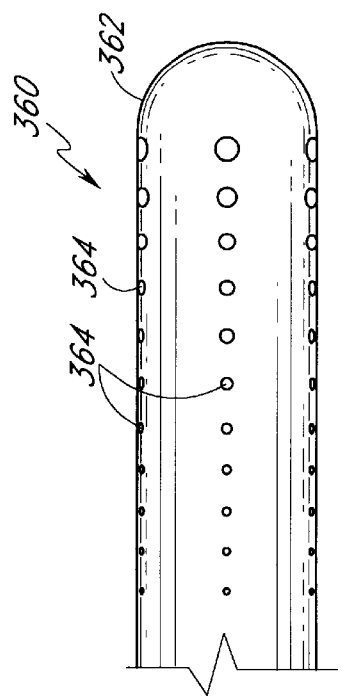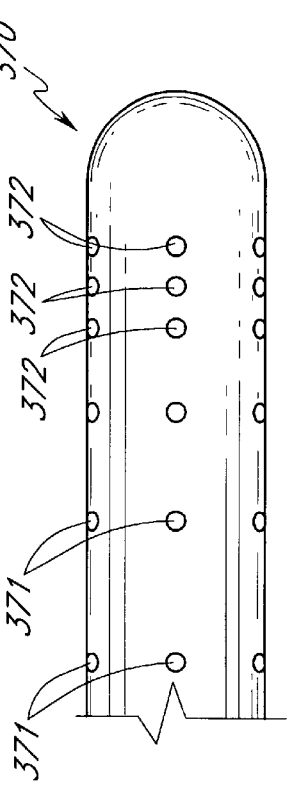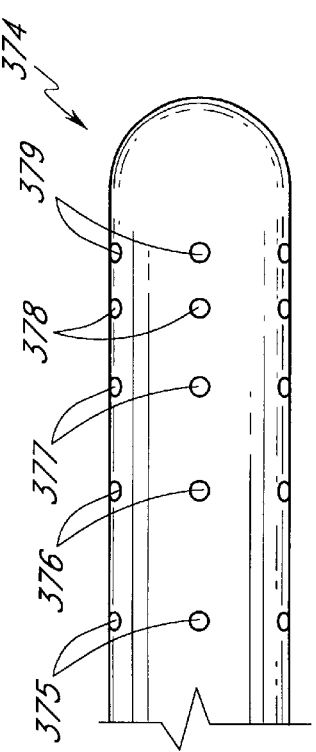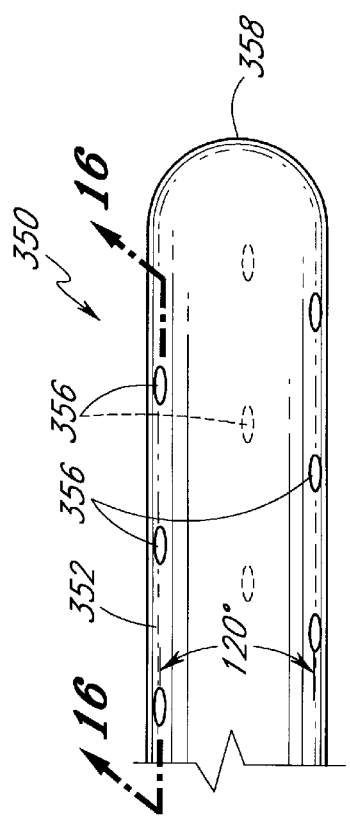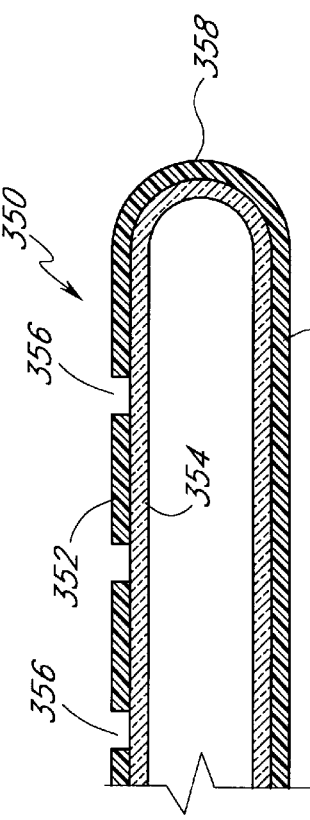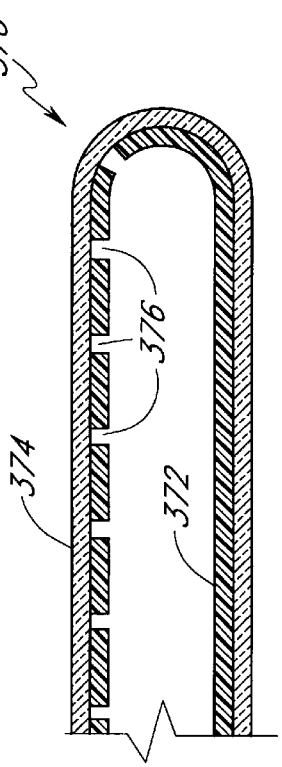

METHOD OF FLUID DELIVERY AND CATHETERS FOR USE WITH SAME

RELATED APPLICATIONS

This application is a continuation-in-part of International application no. PCT/US00/19746 filed Jul. 18, 2000 which is a continuation-in-part of U.S. application Ser. No. 09/363,228 filed Jul. 19, 1999.

BACKGROUND OF THE INVENTION

1. Field of the Invention

This invention relates to liquid dispensing systems, and more specifically to a catheter-based system for infusing a liquid into the body of a patient, and most specifically to a pain management system which administers a post-operative drug to a wound site of a patient through a catheter that delivers fluid medication uniformly and at a known rate across an infusion section of the catheter.

2. Description of Related Art

Patient trauma, pain and discomfort resulting from surgery or other procedures is routinely managed through the administration of narcotics or non-narcotic drugs. Narcotics are generally disfavored as a pain management system because they affect the entire physical and mental well-being of the patient rather than only the local physical area of concern. Narcotics also have a variety of undesirable side effects, such as nausea, vomiting, bowel retention, respiratory depression, inhibition of the cognitive process, alteration of appetite, and potentially causing addiction. If used, narcotics can be administered through a variety of known ways, such as intramuscular injection, epidural injection, intravenous injection or orally.

Post-operative pain management is commonly addressed by administering non-narcotic drugs to the patient. Typically, the drug is administered directly into the epidural space of the patient for a period of several days following surgery. However, administering narcotics or non-narcotic drugs into the patient often necessitates monitoring by hospital staff and additional hospital stay due to the side effects of the drugs or because patients cannot be sent home with the required equipment to administer the drugs.

One direct-site drug administration procedure involves using a syringe and needle several times per day to inject the drug at or near the site where the surgeon made the incision through the patient's skin, with several needle pierces made during each dose application. Because many needle pierces are cumulatively made at or near the sensitive incision site, this administration procedure further aggravates patient trauma, pain and discomfort.

Another direct site drug administration procedure involves placing a drug directly into a wound site prior to a surgeon closing the wound. However, this procedure typically lasts only approximately four to six hours and patients often need pain management at a wound site for far in excess of this time period.

A need therefore exists for a pain management system which reduces patient trauma, pain and discomfort resulting from surgery or other procedures. A need also exists for a drug administration system which does not require repeated needle piercings at or near the sensitive incision site. Additionally, there exists a need for a portable drug administration system that a patient can take home to reduce the patient's hospital stay. Finally, there is a need for a dispensing system that dispenses a liquid from a first location to a second location at a predictable and known rate.

In addition to the prior art limitations and needs described above, there are also certain limitations with infusion catheters that are often used in pain management systems. Infusion catheters, which are well known in the art, generally include a flexible hollow tube inserted into some region of the anatomy. The tube typically contains one or more axial lumens within which the fluid may flow. The proximal end of the catheter tube is connected to a fluid source from which fluid is introduced into the catheter tube. The fluid flows within one of the lumens under pressure supplied at the proximal end of the tube. For each lumen, there are commonly provided one or more exit holes along an infusion section near the distal end of the tube, for fluid to exit the tube. Such exit holes may be created by piercing the side wall of the hollow tube.

In certain medical conditions, it is advantageous to deliver fluid medication to a plurality of sites within a wound area. For instance, some wounds which require pain medication may be in communication with many nerve endings, rather than a single nerve trunk. One example of such a wound is a surgical incision. As stated above, it is known to provide a plurality of exit holes through which the fluid medication exits the catheter tube. The exit holes may be provided at various axial and circumferential positions along the catheter tube in order to control the position of the medication delivery sites. An example of a catheter having this configuration is disclosed in U.S. Pat. No. 5,800,407 to Eldor. Also, in some cases it is desirable to deliver such medication under low pressure, so that the fluid is delivered at a relatively low rate. For example, some pain medications must be delivered slowly to avoid toxicity and other side effects. Furthermore, in many cases it is desirable to dispense fluid medication at a substantially uniform rate throughout the infusion section of the catheter, so that the medication is evenly distributed throughout the wound area.

Unfortunately, a limitation of prior art catheters with multiple exit holes, such as the catheter taught by Eldor, is that during low pressure delivery of fluid medication the fluid tends to exit only through the exit hole(s) nearest to the proximal end of the infusion section of the catheter tube. This is because fluids flowing through a tube more readily exit through the exit holes offering the least flow resistance. The longer the flow path followed by the fluid in the lumen, the higher the flow resistance and pressure drop experienced by the fluid. The most proximal holes offer the least flow resistance and pressure drop. Therefore, the fluid tends to exit the catheter tube primarily through these exit holes. As a result, the fluid medication is delivered only to a small region within the wound area. The tendency of the fluid to undesirably flow only through the most proximal exit holes depends upon the hole size, the total number of exit holes, and the flow rate. As the hole size or number of holes increases, the fluid becomes more likely to exit only through the most proximal holes. Conversely, as the flow rate increases, the fluid becomes less likely to do so.

The tendency of the fluid to undesirably exit only through the most proximal holes of the catheter can in some cases be overcome by increasing the flow rate or pressure of the fluid, which causes the fluid to flow through more of the exit holes of the catheter. Indeed, if the flow rate or pressure is sufficiently high, the fluid will flow through all of the exit holes. However, sometimes it is medically desirable to deliver medication at a relatively slow rate, i.e., at a low pressure. Also, even in those cases in which high-pressure fluid delivery is acceptable or desirable, prior art catheters do not provide for uniform fluid delivery along the infusion section of the catheter. Rather, the flow rate through the exit holes nearer to the proximal end of the infusion section tends to be greater than that through the exit holes nearer to the distal end. This is because the fluid passing through the more proximal holes experiences a lower flow resistance and pressure drop. In contrast, the fluid flowing through the more distal holes experiences greater flow resistance and pressure drop, and consequently exits at a lower flow rate. The further distal the hole, the lower the exit flow rate of the fluid. As a result, there is an uneven distribution of medication throughout the wound area.

In another known type of infusion catheter, several lumens are provided within a catheter tube. For each lumen, one exit hole is provided by piercing a hole within the wall of the tube. The exit holes are provided at different axial positions along the infusion section of the catheter tube. In this manner, fluid medication may be delivered to several positions within the wound area. While this configuration offers improved fluid distribution, it has some disadvantages. One disadvantage is that the fluid flow rates through the exit holes are not equal, since the more distal exit holes offer a greater flow resistance for the same reasons discussed above. Another disadvantage is that the number of lumens, and consequently the number of fluid exit holes, is limited by the small diameter of the catheter tube. As a result, fluid may be delivered only to a very limited number of positions within the wound area. Yet another disadvantage is that the proximal ends of the lumens must be attached to a complicated manifold which increases the cost of manufacturing the catheter.

An example of a catheter providing a more uniform dispensation of fluid medication throughout an infusion section of the catheter is illustrated by U.S. Pat. No. 5,425,723 to Wang. Wang discloses an infusion catheter including an outer tube, an inner tube concentrically enclosed within the outer tube, and a central lumen within the inner tube. The inner tube has a smaller diameter than the outer tube, so that an annular passageway is formed therebetween. The outer tube has a plurality of evenly spaced exit holes defining the infusion section of the catheter. In use, fluid flowing within the central lumen passes through strategically positioned side holes within the side walls of the inner tube. In particular, the spacing between adjacent side holes decreases along a length of the inner tube to induce more fluid to pass through the more distal side holes. The fluid then flows longitudinally through the annular passageway before exiting through the exit holes in the outer tube wall. In the annular passageway, the fluid can flow in a distal or proximal direction, depending on the location of the nearest exit hole in the outer tube. This configuration is provided to induce a more uniform exit flow rate of fluid from the catheter.

Unfortunately, the Wang catheter is only effective for relatively high pressure fluid delivery. When used for relatively low pressure fluid delivery, the catheter disclosed by Wang does not provide uniform dispensation of fluid. Instead, the fluid tends to exit through the side holes of the inner and outer tubes that are nearest to the proximal end of the infusion section of the catheter, since these holes offer the least flow resistance. Even for high pressure fluid delivery, there are several limitations of this design. One limitation is that the concentric tube design is relatively complex and difficult to manufacture. Both tubes must be flexible enough to permit maneuverability through an anatomical system, yet the annular passageway must remain open so that fluid may flow uniformly therein. Another limitation is that the annular passageway may be disturbed if there is a bend in the infusion section of the tube. A bend in the catheter may deform the annular passageway or even cause the inner and outer tubes to come into contact. This can cause an uneven fluid pressure within a longitudinal cross-section of the annular passageway, resulting in non-uniform fluid delivery.

Thus, there exists a need for an improved pain management system, using an improved infusion catheter for delivering fluid medication uniformly along its infusion section. It should come in a relatively simple, easy to manufacture design which is effective for both high flow rate and low flow rate fluid delivery. Furthermore, it is recognized that a particular class of catheters, such as the Wang catheter, may provide uniform fluid delivery only at high fluid pressure or flow rates. However, there is a need for an infusion catheter belonging to this class that has a relatively simple, easy to manufacture design and can maintain uniform fluid delivery while bent or otherwise physically deformed.

SUMMARY OF THE INVENTION

One aspect of the present invention provides a portable pain management system for the post-operative infusion of a non-narcotic local drug to the wound site of a patient. The system achieves this function without piercing the sensitive incision site and instead pierces the patient's skin at a pierce site at a distance from the incision site.

Briefly stated, the system provides a pump connected to medical tubing. The medical tubing, in turn, is connected to a unique catheter. The catheter is inserted into the body of a patient at a pierce site and advanced within the patient's body to the wound site. A clamp, filter, and/or flow controller may be positioned along a portion of the medical tubing to assist in providing the drug at a predicable and known rate to the wound site.

In operation, when the infusion pump is loaded with the drug, the pump imparts a pressure on the drug. This constant pressure causes the drug to flow from the pump, through the medical tubing, through the catheter, into the patient's body, and to the wound site.

The procedure of inserting the unique catheter into the patient's body may be performed prior to loading the pump with the drug. Alternatively, the catheter may be inserted after the pump is loaded with the drug. In accordance with one preferred procedure, a guide needle is placed within an introducer tubing. After that, the needle/tubing assembly is pierced through the patient's skin at a site spaced from the incision site. The guide needle is then withdrawn and discarded, leaving the introducer tubing in place partially under the patient's skin, so the unique catheter can be threaded through the introducer tubing and advanced to the wound site. The introducer tubing is then withdrawn and discarded while the unique catheter remains in place to administer the drug to the wound site. Preferably, the introducer tubing may be peeled off of the unique catheter into two pieces so that the unique catheter may be integrally secured to a hub prior to use.

Insertion of the guide needle at a remote pierce site rather than at the incision site is advantageous for many reasons. The spaced insertion location keeps the incision site cleaner and decreases the potential for infection at the incision site. Further, the remote insertion location assists in the proper formation of scar tissue at the incision site, which would otherwise be hindered by insertion of a needle through the incision site. This insertion technique also provides a more secure base through which the catheter enters into the patient's body and minimizes catheter removal problems. One skilled in the art will understand that other advantages to using this remote insertion location exist.

Accordingly, it is another principle object and advantage of the present invention to overcome some or all of these limitations by providing an improved catheter for delivering fluid medication to the wound area of an anatomical region.

In accordance with one embodiment of the present invention, the catheter provides for the uniform delivery of fluid across an anatomical region, and comprises an elongated tubular member made of a porous membrane. The membrane is sized to be inserted through a subcutaneous layer surrounding the anatomical region, such as a person's skin. The membrane is configured so that a fluid introduced under pressure into an open end of the tubular member will flow through side walls of the tubular member at a substantially uniform rate along a length of the tubular member. The present invention also provides a method of uniformly delivering fluid throughout an anatomical region, comprising the steps of inserting the elongated tubular member into the anatomical region and introducing a fluid under pressure into an open end of the tubular member.

Another embodiment of the present invention provides a catheter and method for the uniform delivery of fluid throughout an anatomical region. The catheter comprises an elongated support and a porous membrane wrapped around the support. The support is configured so that one or more lumens are formed between the support and the membrane. Alternatively, the support may be a tubular member having a plurality of holes therein. The method comprises the steps of inserting the above-described catheter into the anatomical region and introducing a fluid under pressure into the proximal end of at least one of the lumens. Advantageously, the fluid passes through the membrane at a substantially uniform rate into the anatomical region. The present invention further provides a method of manufacturing this catheter comprising the steps of forming an elongated support and wrapping a porous membrane around the support so that one or more lumens are formed between the support and the membrane.

Another embodiment of the present invention provides a catheter and method for the uniform delivery of fluid throughout an anatomical region. The catheter comprises an elongated tube including a plurality of exit holes along a length thereof and a tubular porous membrane concentrically enclosed within the tube. The tube and membrane define a lumen. The method comprises the steps of inserting the above-mentioned catheter into the anatomical region and introducing a fluid under pressure into the proximal end of the lumen so that the fluid advantageously passes through the membrane and the exit holes at a substantially uniform rate into the anatomical region. The present invention further provides a method of manufacturing his catheter, comprising the steps of forming an elongated tube, providing a plurality of exit holes along a length of the tube, forming a tubular porous membrane, and concentrically enclosing the tubular porous membrane within the tube so that the tube and membrane define a lumen.

Yet another embodiment of the present invention provides a device and method for the uniform delivery of fluid throughout an anatomical region. The device is advantageously simple and easy to manufacture, comprising an elongated catheter having a plurality of exit holes along a length thereof. The exit holes may serve as the flow-restricting orifice. Alternatively, a flow-restricting orifice may be provided elsewhere within the catheter or proximal to the catheter. The exit holes may gradually increase in size along the length of the catheter, so that the largest exit hole is further distal than the smallest exit hole. Alternatively, the holes can be laser drilled and be of approximately the same size. Advantageously, a fluid flowing under pressure within the catheter will flow through substantially all of the exit holes at a substantially equal rate. The method comprises the steps of inserting the catheter into the anatomical region and introducing a fluid under pressure into the proximal end of the catheter. The fluid flows through the exit holes and enters the anatomical region, advantageously flowing through substantially all of the exit holes at a substantially equal rate. The present invention further provides a method of manufacturing this device, comprising the steps of forming an elongated catheter and providing a plurality of exit holes along a length of the catheter in a manner so that the exit holes gradually increase in size along the length of the catheter from the proximal end to the distal end thereof.

Yet another embodiment of the present invention provides a catheter and method for delivering fluid medication to an anatomical region. The catheter comprises a tube, a "weeping" tubular coil spring attached to a distal end of the tube, and a stop closing a distal end of the spring. The tube and spring each define a portion of a central lumen. The spring has adjacent coils in contact with one another so that fluid within the spring and below a threshold dispensation pressure is prevented from exiting the lumen by flowing radially between the coils. The spring has the property of stretching when the fluid pressure is greater than or equal to the threshold dispensation pressure permitting the fluid to be dispensed from the lumen by flowing radially between the coils, i.e. "weeping" through the spring. Alternatively, the fluid may weep through imperfections in the spring coil. Advantageously, the fluid is dispensed substantially uniformly throughout the length and circumference of a portion of the spring. In use, fluid is introduced into an open proximal end of the tube, allowed to flow into the spring, and brought to a pressure greater than or equal to the threshold dispensation pressure so that the fluid weeps through the spring.

Yet another embodiment of the present invention provides a catheter and method for delivering fluid medication to an anatomical region. The catheter comprises a distally closed tube and a "weeping" tubular coil spring, as described above, concentrically enclosed within the tube. A plurality of exit holes are provided in side walls along a length of the tube, defining an infusion section of the tube. The spring is enclosed within the infusion section so that a lumen is defined within the tube and spring. In use, fluid is introduced into a proximal end of the tube, allowed to flow into the spring, and brought to a pressure greater than or equal to the threshold dispensation pressure of the spring so that the fluid is dispensed from the lumen by weeping through the spring and then flowing through the exit holes of the tube.

Yet another embodiment of the present invention provides a catheter comprising an elongated tube and a solid flexible member positioned within the tube. The tube has a closed distal end and a plurality of exit holes in side walls of the tube. The exit holes are provided along a length of the tube defining an infusion section of the catheter. The tube is sized to be inserted into an anatomical region. The member is positioned within the tube and is sized so that an annular space is formed between the tube and the member. The member is formed of a porous material. Advantageously, the catheter is configured so that a fluid introduced into a proximal end of the tube will flow through the exit holes at a substantially uniform rate throughout the infusion section.

In yet another embodiment, the present invention provides a catheter comprising an elongated tube having a plurality of exit slots in side walls of the tube. The slots are provided along a length of the tube defining an infusion section of the catheter. The exit slots are oriented generally parallel to the longitudinal axis of the tube. Advantageously, the tube is configured so that a fluid flowing therein will flow through substantially all of the exit slots at a substantially equal rate. In one optional aspect, the slots increase or decrease in length from the proximal to the distal ends of the infusion section.

In yet another embodiment of the present invention, exit holes along the catheter may be unevenly spaced to achieve more even flow of fluid throughout the infusion section of the catheter. For example, the proximal end of the infusion section may have a first distance between adjacent holes and the distal end of the infusion section may have a second, shorter distance between adjacent holes. Alternatively, the distance between adjacent holes can decrease in the distal direction.

For purposes of summarizing the invention and the advantages achieved over the prior art, certain objects and advantages of the invention have been described hereinabove. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

Further aspects, features and advantages of the present invention will become apparent from the following drawings and detailed description intended to illustrate but not to limit the concepts of the invention.

BRIEF DESCRIPTION OF THE DRAWINGS

FIG. 3A is a side elevational view of a guide needle surrounded by introducer tubing;

FIG. 3B is a side elevational view of a guide needle surrounded by a unique, peel-away introducer tubing;

FIG. 4 is a schematic view of a pierce site of the patient of FIG. 1, showing the needle/tubing assembly of FIG. 3 pierced through the patient's skin at the pierce site, the pierce site being spaced from an incision site;

FIG. 5 is a schematic, cross sectional view, showing the needle/tubing assembly of FIG. 3 pierced through the patient's skin at the pierce site and extending to the wound site;

FIG. 6 is a view similar to FIG. 5, showing the guide needle withdrawn from the introducer tubing and a portion of the introducer tubing remaining in place partially under the patient's skin;

FIG. 9 is a schematic, cross sectional view, showing the downstream end of the catheter with a plurality of holes formed thereon; and FIG. 10 is a view similar to FIG. 9, showing an alternative downstream end of the catheter;

FIG. 11 is a schematic side view of a catheter having features and advantages in accordance with the present invention;

FIG. 12 is a sectional view of the catheter of FIG. 11, taken along line 12—12 of FIG. 11;

FIG. 13 is a sectional view of the catheter of FIG. 11, taken along line 13—13 of FIG. 11;

FIG. 14 is a perspective view of the end portion and support beam of the catheter of FIG. 11, illustrating a cross-section taken along line 14—14 of FIG. 11;

FIG. 15 is a side view of a catheter having features and advantages in accordance with another embodiment of the present invention;

FIG. 16 is a cross-sectional view of the infusion section of the catheter of FIG. 15 taken along line 16—16 of FIG. 15;

FIG. 17 is a cross-sectional view of a catheter having features and advantages in accordance with another embodiment of the present invention;

FIG. 18A is a side view of a catheter having features and advantages in accordance with another embodiment of the present invention;

FIG. 18B is a side view of a catheter having features and advantages in accordance with another embodiment of the present invention;

FIG. 18C is a side view of a catheter having features and advantages in accordance with another embodiment of the present invention;

DETAILED DESCRIPTION OF THE PREFERRED EMBODIMENTS

The preferred embodiment of the liquid dispensing system is illustrated in the context of an exemplary pain management system which administers a drug into the body of a patient that has undergone arthroscopic shoulder surgery. However, the pain management system can be used with any type of surgical procedure, and on any portion of the patient's body, such as knees, elbows and the like. The principles of the present invention, moreover, are not limited to administering a drug or infusing a liquid into the body of a patient. Instead, it will be understood by one of skill in the art, in light of the present disclosure, that the dispensing system disclosed herein can be used to introduce or remove other materials from a wound site or other area within a patient.

To assist in the description of the system and method of use disclosed herein, the following terms are used. The term "distal" refers to a site that is away from a specified site. The term "proximal" refers to a site that is close to a specified site. Expressed alternatively, a site termed "proximal" is measurably closer to a specified reference point than a site termed "distal." The term "downstream" refers to directional movement of the liquid drug from the infusion pump to the wound site. An object or site referred to as "downstream" of another object or site means that the "downstream" object or site is proximal the wound site relative to the other object or site. Similarly, an object or site referred to as "upstream" to another object or site means that the "upstream" object or site is proximal the infusion pump site relative to the other object or site. Expressed alternatively, the "downstream" object is proximal the wound site and the "upstream" object is distal the wound site.

The "wound site" is the area within the body of the patient where the surgical procedure was performed. The "incision site" is the area where the surgeon entered through the patient's skin to arrive at the wound site. The incision site need not be made by the surgeon, for example, a patient may have an open wound (e.g. knife incision) through which the surgeon arrives at the wound site. The "pierce site" is the site where the patient's skin is pierced to allow the catheter to extend therethrough and arrive at the wound site to administer the drug.

System Components

Figure 1:
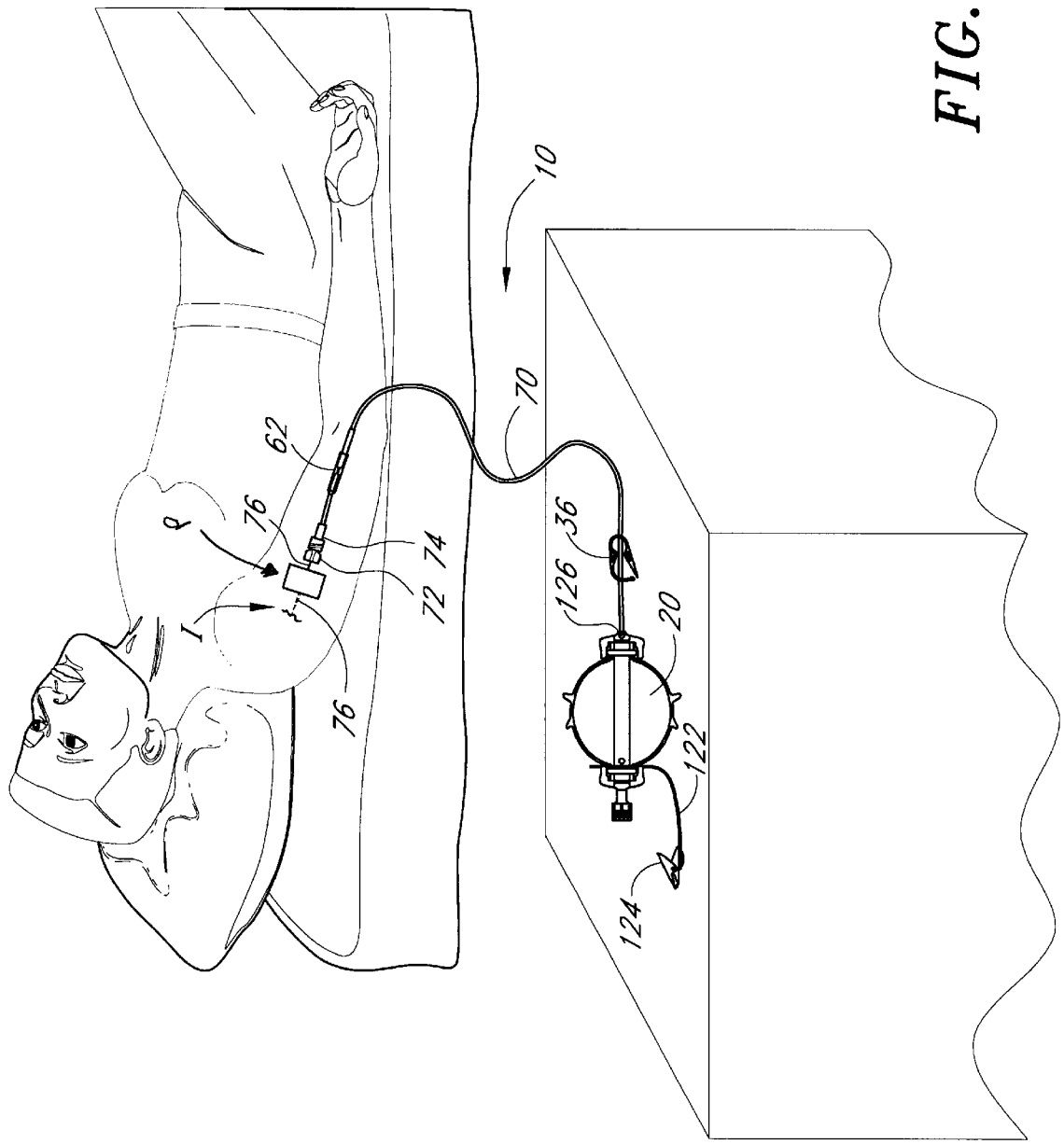
FIG. 1 is a perspective view of the liquid dispensing system of the present invention, illustrating a general orientation of the system when used with a post-surgical medical patient having a wound.
Figure 2:
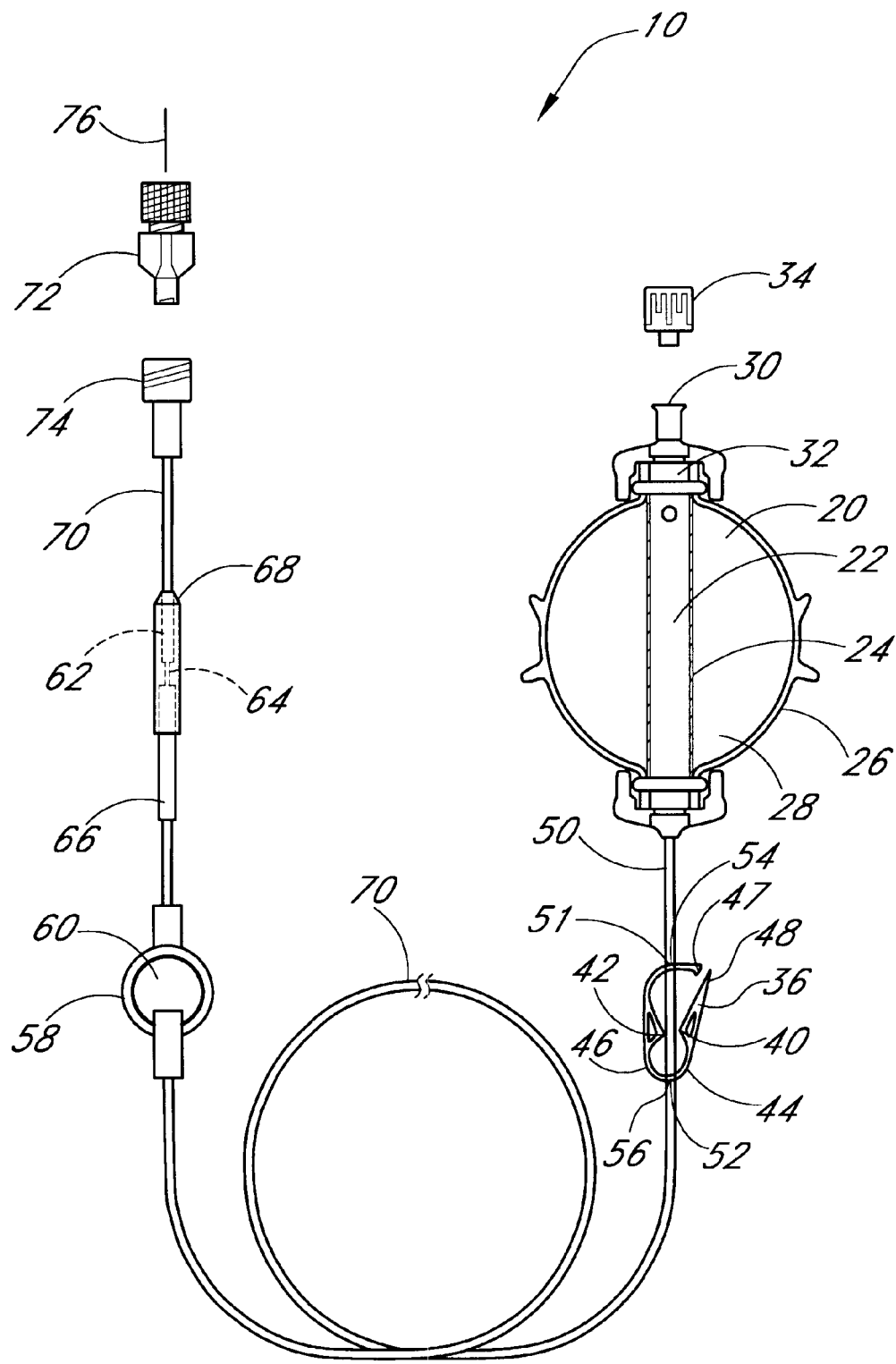
FIG. 2 is a top plan view, showing additional system elements.

FIGS. 1 and 2 illustrate a liquid dispensing system 10 employing a pump 20 connected to an inlet port 30 on one end and to medical tubing 70 on the other end. The medical tubing 70, in turn, is connected to a catheter 76. The catheter 76 is inserted into the body of a patient at a pierce site P, adjacent an incision site I, and advanced within the patient's body to an interior wound site W (not shown in FIG. 1), thereby allowing application of the drug to the wound site W. A clamp 36, filter 58, and/or flow controller 62 may be positioned along a portion of the medical tubing 70 to assist in providing the drug to the wound site W at a predicable and known rate.

Referring to FIG. 2, the infusion pump 20 preferably accommodates up to about 500 ml of drug and more preferably up to about 100 ml. The pump 20 can impart pressure on the drug, causing the drug to flow out of the pump at a predictable rate. The illustrated pump has an inner core 22, elastomeric bladder 24 and a housing 26, which define a reservoir 28. The illustrated pump 20 is described in U.S. Pat. No. 5,284,481 assigned to I-Flow Corporation, which is hereby incorporated by reference. However, a variety of other conventional infusion pumps may be used, so long as they can impart a pressure on the drug. For example, the pumps described in U.S. Pat. Nos. 5,080,652 and 5,105,983 both assigned to I-Flow Corporation, which are hereby incorporated by reference may be used, as well as other suitable electronic or mechanical pumps offered by many other manufacturers.

An inlet valve or injection port 30 at an upstream end 32 of the infusion pump 20 delivers the drug into the inner core 22 of the pump 20. The injection port 30 is sized and configured to removably interconnect with a conventional syringe (not shown) to load the drug into the infusion pump 20. The interconnection between the injection port 30 and the syringe may be achieved by mating threadings, tapers, ends or other suitable configurations, as will be understood by one of skill in the art. When not connected to the syringe, the injection port 30 is sealed and may be protected by an injection cap 34 connected to the injection port 30.

A clamp 36 arranged downstream of the infusion pump 20 can compress the medical tubing 70, so that fluid flow is occluded. The illustrated embodiment shows the clamp 36 having a pair of opposing projections 42 and 40 respectively extending from a first wall 46 and a second spaced wall 44. At least one of the walls is sufficiently flexible so that the walls can be moved closer together. When the walls are advanced sufficiently close, the projections 40 and 42 are advanced to a position in which the space between them is reduced sufficient to pinch the medical tubing 70 and occlude fluid flow. A recess 47 is preferably formed on the first wall 46 and an extension 48 is preferably formed on the second wall 44. When the walls 46 and 44 are advanced sufficiently close to occlude fluid flow through the medical tubing 70, the recess 47 and extension 48 removably interlock to maintain the occlusion. The arrangement of the recess 47 and extension 48 may be reversed, and other suitable interlocking means may also be used. First and second openings 51 and 52 can be arranged on opposing ends 54 and 56 of the clamp 36 so it can slide along a length of the medical tubing 70 and occlude various portions of the tubing. As will be understood by one of skill in the art, a variety of other conventional clamps can be used to achieve the occlusion function. For example, roller clamps, stopcocks and other clamps known in the industry may be used to occlude flow of fluid from the pump 20 through the tubing 70.

Still referring to FIG. 2, a filter 58 downstream of the clamp 36 separates the drug from contaminates and other undesired particles that may be found within the drug. The filter 58 also eliminates air from the fluid path. The illustrated embodiment shows the filter 58 having a porous membrane 60 which captures the contaminates and other undesired particles, while allowing the drug to pass through the porous membrane 60. The capture may be performed by a variety of methods to include physical capture, where the size of the porous member 60 selectively performs the capture; chemical capture, where the composition of the porous member 60 selectively performs the capture; or other suitable capture methods which separate the drug from contaminates and other undesired particles.

A flow controller 62 arranged downstream of the filter 58 assists in maintaining a predicable and known flow of the drug to the wound site W. At least a portion of the flow controller 62 has a micro-bore cannula 64 with a predetermined constant lumen radius and a predetermined constant lumen length. By this configuration, a dam effect is provided where the upstream end 66 of the cannula 64 may be analogized to a reservoir, and the downstream end 68 of the cannula 64 enjoys a predicable, known flow rate. However, any other suitable device may be used to perform the flow control function including, but not limited to, the catheter itself.

Although FIG. 2 shows the clamp 36, filter 58 and flow controller 62 arranged on the medical tubing 70, these elements are merely advantageous to use and are not required, as shown in FIG. 1, which illustrates only the optional clamp 36 and flow controller 62 in use. FIG. 2 also shows the clamp 36 upstream of the filter 58, which is upstream of the flow controller 62. However, this particular arrangement is merely exemplary. FIG. 2 further shows only a single clamp 36, filter 58 and flow controller 62 used, however, a plurality of any of these elements may be used. Moreover, the clamp 36, filter 58 and/or flow controller 62 may be integral with the pump 20. Thus, any combination of these elements may be present in the fluid tubing 70.

Still referring to FIG. 2, medical tubing 70 extends from at least the downstream end of the infusion pump 36 to at least an upstream end of a catheter connector 72 (detailed below). The illustrated embodiment shows the medical tubing 70 as a one-piece assemblage formed with the infusion pump 20, clamp 36, filter 58 and flow controller 62. However, the assembly need not be unitary. Rather, one or more connectors 74, such as a conventional luer-lock connectors, may be used to modularly connect one or more segments of medical tubing 70 and/or elements of the system to each other. Also, the medical tubing 70 need not have a uniform diameter.

The catheter connector 72 at the downstream end of the medical tubing 70 is illustrated as a conventional Toughy Borst connector. The connector 72 connects the distal end of the tubing 70 (via a luer lock 74 attached to the distal end of the tubing 74) to the proximal end of a catheter 76.

In another improved method, the catheter 76 may be secured to a hub (not shown) prior to connection of the hub to the distal end of the tubing 70. This arrangement is advantageous so that a physician or healthcare worker does not need to accomplish the added step of securing the catheter 76 to the connector 72.

In one example, a 20 gage catheter 76 having a length of about 100 cm was found to be satisfactory. Of course, the catheter may be of any length desired by the healthcare worker. The downstream end of the catheter desirably has a plurality of holes 77 to assist in dispensing the drug throughout the wound site W. See FIGS. 9 and 10. The holes 77 are arranged along a length of the catheter 76 that can range from about 1–200 cm, depending on the length of the wound site W. The diameter of the holes 77 may be of varied size relative to the downstream end of the catheter 76 to assist in equal distribution of the drug along the wound site W. Additional embodiments of the catheter are discussed in detail below. As those of skill in the art can appreciate, the methods described herein may be used with any of the catheter embodiments discussed herein. For example, the method may be used with any catheter described and illustrated in FIGS. 9–31 or with any other catheter manufactured by any entity.

Alternatively, instead of connecting the pump 20 to the tubing 70 and the tubing 70 to the catheter 76. The pump 20, tubing 70 and catheter 76 can be bonded or otherwise permanently secured to comprise a unitary one-piece member. Unitary construction presents several advantages. For example, unitary construction obviates improper connection of the luer-lock connector 74 and Toughy Borst connector 72 or catheter hub. That is, if the connectors 72, 74 are connected loosely, fluid leakage or accidental disconnection of components may occur. Similarly, if the connectors 72, 74 are connected too tight, the connector threads may strip. For another example, unitary construction obviates lost or misplaced components. A unitary construction may be preferred if the portable liquid dispensing system 10 is used by a patient at home without the benefit of continuous medical supervision.

Illustrative Catheter Insertion Methods

Referring to FIGS. 3–8, a preferred procedure to insert the catheter 76 into the patient's body at the pierce site P, spaced from the incision site I, and advance the catheter 76 to the wound site W is illustrated.

Referring to FIGS. 3A and 4, a guide needle 78 comprises a conventional medical needle or rod having a pointed end 80 sufficiently sharp to pierce and penetrate the patient's skin. The guide needle 78 may be hollow or solid without any lumen therethrough. An introducer tubing 82 has a diameter sufficient to allow the guide needle 78 to be placed therein. The introducer tubing or conduit 82 is sufficiently rigid so that it can extend through the pierce site P and into the patient's body without significantly bending away from the guide needle 78 upon penetration through the skin.

At least a portion of the guide needle 78 is placed within at least a portion of the introducer tubing 82 to form a needle/tubing assembly 84. When the needle/tubing assembly 84 is formed, the end 80 of the guide needle 78 preferably extends beyond the end 86 of the introducer tubing 82 so that the end 80 of the guide needle 78 initially pierces the patient's skin at the pierce site P and then the end 86 of the introducer tubing 82 extends through the pierce site P.

The needle/tubing assembly 84 cooperates so that when the guide needle 78 and introducer tubing 82 pierce the skin and are advanced into the patient to form a passage, neither the guide needle 78 nor introducer tubing 82 appreciably move relative to each other, yet, when the guide needle 78 is withdrawn, the guide needle 78 separates from the introducer tubing 82 and at least a portion of the introducer tubing 82 remains within the patient. This cooperation can be achieved in a variety of ways. One way is to provide a taper 88 on the introducer tubing 82 so that the downstream end 90 has a smaller diameter than the upstream end 92. Thus, when the needle/tubing assembly 84 is advanced, the downstream outer diameter 94 of the guide needle 78 contacts the downstream inner diameter 90 of the introducer tubing 82, yet when the needle/tubing assembly 84 is withdrawn, the upstream outer diameter 96 of the guide needle 78 does not contact the upstream inner diameter 92 of the introducer tubing 82. Another way this cooperation can be achieved is to arrange an extension or stop 98 on the downstream end of the introducer tubing 82. The stop 98 prevents a protuberance 100 formed on the guide needle 78 and upstream of the stop 98 from advancing relative to the introducer tubing 82 (the protuberance 100 has a larger diameter than the stop 98), yet does not prevent the guide needle 78 from being withdrawn from the introducer tubing 82.

Referring to FIGS. 4 and 5, once the guide needle 78 is placed within the introducer tubing 82, the needle/tubing assembly 84 is then pierced through the patient's skin at the pierce site P. The end 80 of the guide needle 78 provides a clean skin pierce. The guide needle 78 preferably pierces the skin at an angle to assist in providing a clean pierce of the resilient skin. Use of the introducer tubing 82, rather than only the guide needle 78 is preferred, because the introducer tubing 82 assists in threading the catheter 76 into the patient's body.

The pierce site P is sufficiently close to the wound site W so that when the introducer tubing 82 is advanced from the pierce site P to the wound site W, it is not snagged, blocked or otherwise inhibited from reaching the wound site W. The pierce site P is, however, sufficiently far from both the wound site W and the incision site I to diminish the likelihood of infection at the wound site. The distance between the pierce site P and the incision site I will depend on a variety of factors, such as the type of drug used, the size of the needle/tubing assembly 84, and the size and type of wound. In the illustrated procedure, the distance between the pierce site P and the incision site I can range from about 1–10 cm, and more preferably from about 3–5 cm.

After the needle/tubing assembly 84 pierces the skin, it is advanced slightly into the patient's body, as explained below. The distance which the needle/tubing assembly 84 is advanced will depend on a variety of factors, as explained above.

Referring to FIG. 6, after the needle/tubing assembly 84 is in place, the guide needle 78 is withdrawn and safely discarded while the introducer tubing 82 remains in place partially under the patient's skin. The introducer tubing 82 forms a passage through which a catheter 76 may be safely introduced into a wound site.

Figure 7:
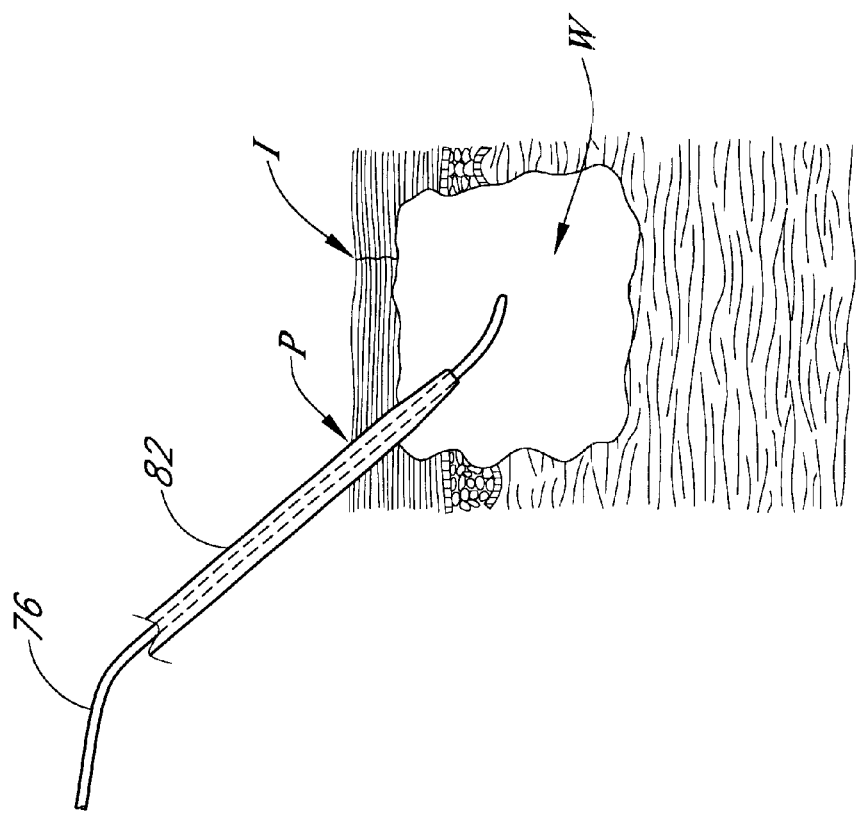
FIG. 7 is a view similar to FIG. 6, showing a catheter threaded through the introducer tubing and advanced along the wound site.

Referring to FIG. 7, after the guide needle 78 is withdrawn from the introducer tubing 82, the catheter 76 is inserted into the introducer tubing 82. The catheter 76 is then advanced from the pierce site P to the wound site W. This advancement can be performed in a variety of ways. The illustrated embodiment shows the introducer tubing 82 extending through the skin and into an end of the wound site W subcutaneously, with the catheter 76 subsequently advancing the length of the wound site W.

In accordance with another technique to advance the catheter 76 from the pierce site P to the wound site W, the catheter 76 is advanced through a hollow or open area (e.g. joint space) in the patient's body which is in contact with the wound site W. The hollow may or may not be filled with a liquid. This technique is similar to the illustrated technique, where the catheter extends through the introducer tubing and then advances through the hollow to the wound site W.

Figure 8:
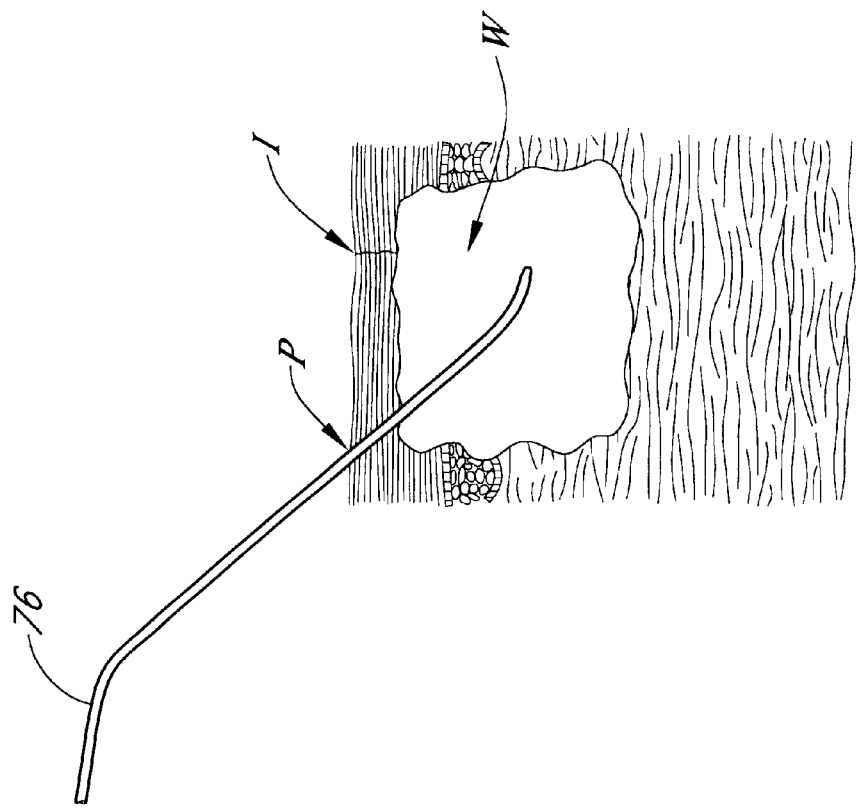
FIG. 8 is a view similar to FIG. 7, showing the introducer tubing withdrawn from the patient's body and the catheter in place at the wound site.

Referring to FIG. 8, after the catheter insertion procedure is performed, the introducer tubing 82 is withdrawn by backthreading it over the catheter 76 and removed from the upstream end of the catheter 76. The upstream end of the catheter 76 is then connected to the connector 72 which is then connected to medical tubing 70.

Alternatively, if a unitary liquid dispensing system 10 is used, a split-introducer tubing 110 (FIG. 3B) is used to replace the introducer tubing 82. That is, the above-described introducer tubing 82 cannot be used with a unitary system because the introducer tubing 82 cannot be back-threaded off of the catheter 76 when the catheter 76 is permanently attached to a hub which will typically have a larger diameter than the tubing 82 so that the hub may be connected to the tubing 70.

FIG. 3B illustrates a split-introducer or conduit 110 that advantageously overcomes the backthreading requirement. The split-introducer 110 is configured similar to the above-described introducer tubing 82, however, the split-introducer 110 further comprises one or more hand-grip portions. The illustrated embodiment shows a pair of opposing hand-grip portions 112, 114 bonded to opposing sides of the split-introducer 110. The hand-grip portions 112, 114 are sized and configured so that a person can grasp them to pull the split-introducer 110 apart into opposing portions 116, 118. Thus, in practice, once the catheter 76 has been threaded through the introducer tubing or conduit 110 to the desired location, the introducer tubing 110 is withdrawn from the patient while holding the catheter 76 in place. Once the introducer tubing 110 is removed from the body of a patient, the introducer 110 is split by a user into two portions or peeled away from the catheter 76 and discarded.

The provision of a split introducer is advantageous so that the healthcare worker does not need to thread the proximal end of the catheter 76 into a connector 72. Often, healthcare workers are concerned that tightening the connector 72 too tightly around the catheter 76 will occlude the catheter 76 and not permit fluid to flow therethrough. Thus, often healthcare workers do not tighten the connection sufficiently between the connector 72 and catheter 76 allowing fluid to leak from the system. As a result, it is preferable to have a catheter connected to a hub or connector 72 prior to insertion of the catheter through the introducer tubing 110. The introducer tubing 110 eliminates the step of securing the catheter 76 to the hub or connector 72, thereby eliminating the risk of catheter malfunction or introduction of contaminants which could enter the patient and cause harm.

The present invention contemplates that any conduit known to those of skill in the art may be used in place of the introducer tubing 82 or the split introducer 110. Any such conduit is deemed to be within the scope of the present invention.

A defined pattern of reduced strength 120 is preferably used to direct the separation of the split-introducer portions 116, 118 when the split-introducer 110 is pulled apart. The defined pattern of reduced strength 120 can be embodied in a variety of configurations, such as one or more score lines, or, as shown in the illustrated embodiment, as a portion of the split-introducer 110 having a thickness less than the thickness of another portion of the split-introducer 110.

One prior art method of introducing a catheter 76 to a wound site W includes using an introducer needle with a sharp point which is inserted through a pierce site P into a wound site W. The catheter 76 is then threaded through the introducer needle to the wound site W. Thereafter, the introducer needle is withdrawn from the patient while holding the catheter in place. This prior art system has many disadvantages. For example, the healthcare worker must thread the needle off of the catheter 76. This increases the chance of needle sticks and transfer of diseases such as AIDS and hepatitis from the patient to a healthcare worker. In addition, because an introducer needle has a sharp point to pierce the skin of a patient, the introducer needle may undesirably rip the catheter 76 which is typically manufactured from a lightweight, flexible material. Thus, by using an introducer tubing 84, 110, several advantages are obtained. First, the guide needle 78 can be safely removed from the introducer tubing and safely discarded without the risk of the introducer needle 78 coming in contact with a healthcare worker. In fact, many manufacturers, including B. Braun, sell introducer needle/introducer catheter assemblies in which the needle is withdrawn from the interior of the introducer catheter without the risk of a healthcare worker being punctured by the needle. That is, the tip of the needle is safely protected prior to the guide needle being fully removed from the introducer tubing. In addition, by removing and discarding the introducer needle 78 before the catheter 76 is introduced to the patient, the risk of ripping the catheter is eliminated. In addition, there is no risk of the catheter snagging on the needle which could cause a portion of the catheter to rip and remain within the patient requiring additional surgery for removal. As a result, it is highly advantageous not to have any contact between the introducer needle 78 and the catheter 76.

Illustrative Use Of the System

Once the catheter 76 is threaded into the wound site W, the system components are connected (if not unitary) and the pump 20 is loaded and the clamp 36 (if used) is opened so that fluid flow within the medical tubing 70 is not occluded. The pressure imparted by the pump 20 causes the drug to flow at a predicable rate from the pump, through the medical tubing 70, through the catheter 76 and into the wound site W. In one example, the portable pain management system described above is provided in a kit which, when assembled, administers drug at a flow rate of about 2 ml/hr for about 48 hours.

Although an injection syringe is preferably used to load the pump 20 with the drug via the injection port 30, other suitable loading methods may be used. For example, a conventional gravity fed medical bag such as those used for intravenous medical operations may be used with an electronic or mechanical pump.

FIG. 1 shows the portable pain management system supported by a table to more clearly show the system elements in context of use. However, the portable system is preferably placed in a location which reduces the obtrusiveness of the system. That is, tangling of the medical tubing 70 or catheter 76 and accidental dislodgment of one or more elements should be minimized. One such preferred location involves tucking the system into a sling attached to the patient's body. Another such preferred location involves coupling the system to a bed, bedrail or bedpost on which the patient lies. Yet another preferred location involves attaching the pump to the patient's clothes through a flexible leash 122 and a clip 124, housing the pump within a fanny pack, or placing the system within any other suitable storage device carried by the patient.

A bolus button 126 or other suitable member may be placed on the system to allow the patient to modify the fluid flow rate. That is, the patient may depress the button 126 to increase or decrease the fluid flow rate, or to initiate fluid flow. The button 126 may also include a conventional cut-off switch that restricts the patient's interaction with the fluid flow rate for safety.

Alternative Catheter Insertion Assemblies

A variety of other catheter insertion assemblies may be used to achieve a pierce site P spaced from the insertion site I and to advance the catheter 76 from the pierce site P to the wound site W.

One disadvantageous assembly includes replacing the needle/tubing assembly 84 with a hollow needle (not shown). In use, the hollow needle pierces the skin and the catheter 76 is then threaded through the hollow portion of the needle to the wound site W. The hollow needle is then withdrawn, leaving the catheter in place at the wound site W. However, because the sharp edges of the hollow needle may rip the catheter when withdrawn, and because healthcare workers may stick themselves with the needle and contract deadly diseases, use of the protective introducer tubing 82, 110 is strongly preferred. Also, if this catheter insertion assembly is used with a unitary liquid dispensing system 10, a needle cannot be used because it cannot be threaded over the hub or connector 72, as will be understood by those of skill in the art.

Another assembly includes replacing the introducer tubing 84 with a snug-fit catheter (not shown). At least a portion of the catheter is resilient and sized to form a snug-fit configuration around a thin needle (not shown). The needle/catheter assembly is then pierced through the patient's skin and advanced to the wound site W. The needle 78 is then withdrawn, leaving the catheter in place at the wound site W. The needle/catheter assembly can advance without appreciable movement relative to each other, yet allows the needle 78 to be withdrawn from the catheter while keeping the catheter in place.

In another alternative embodiment, a split "T peel" needle may be used to introduce the catheter 76 to the wound site W. In this embodiment, the T peel needle is inserted through the skin of a patient a distance from a wound site W and advanced to the wound site W. The catheter is then threaded through the T peel needle into the wound site. Upon withdrawal of the T peel needle, the needle is split and discarded leaving the catheter in place in the wound site W. In this method, the introducer tubing 82, 110 would not be needed.

In another method, the tubing 70 extending from the pump 20 may include a Y-site connector to split the tubing into two branches. Each branch may be placed in fluid communication with a catheter to deliver drugs to a patient. This embodiment is particularly useful when a large wound requires two catheters to provide the drug to the entire wound. Alternatively, this method is useful when two independent wound sites require administration of drugs. Each catheter then may be inserted into a respective wound using the methods disclosed herein.

Moreover, the tubing 70 may include a Y-site connector whereby two pumps containing different liquids may be used to combine the two liquids for administration of both liquids through a single catheter to a wound site W. In this way, two liquids may be administered to a wound site using a single catheter. Of course, by adding additional Y-sites in the tubing 70, more than two catheters and/or two pumps may be used to administer fluids to a patient.

In another embodiment of the invention, the guide needle 78 may be of a protected variety such that the tip of the guide needle is protected upon withdrawal of the needle from the introducer tubing, thus reducing the risk of needle sticks to healthcare workers. By reducing this risk, the risk of disease being transferred from a patient to a healthcare worker is reduced.

Through the use of an introducer tubing 110 or T peel needle, the pump 20, tubing 70 and catheter 76 may be bonded together and sold as a single unit. This unit would be advantageous for several reasons, including, but not limited to, 1) the reduced chance of leakage of the fluid, 2) the reduced risk of a patient becoming infected due to a contaminant entering the system at a connection, and 3) the pump, tubing, catheter arrangement would be easier to use as it would require no assembly. Thus, the use of a combined pump, tubing, and catheter arrangement is within the scope of the present invention.

In the preferred embodiment, the following steps are performed to administer an anesthetic to a wound site W.

First, the pump 20 is filled with the liquid anesthetic. To accomplish this, the clamp 36 is closed to prevent fluid flow through the tubing 70. Next, the protective cap 34 is removed from the introducer port 30 of the pump 20. A syringe filled with the liquid anesthetic is then removably secured to the introducer port 30 and the plunger of the syringe (not shown) is depressed, transferring the fluid from the syringe interior to the interior of the pump 20. This step is repeated as many times as necessary to fill the pump. Preferably, the pump contains a one-way check valve (not shown) to prevent fluid from the pump interior from exiting the pump via the port 30. After the pump is filled with fluid, the cap 34 may be replaced on the port 30. The pump may be filled using any of a variety of techniques known to those of skill in the art.

Optionally, a label may be secured to the pump identifying the liquid within the pump and specific patient information for safety reasons.

Next, the clamp 36 is opened permitting fluid to flow through the tubing 70. Preferably, the tubing may have a distal end cap (not shown) which can be removed to permit fluid to prime the tubing 70. Once the fluid medication has filled the entire tubing 70 and reached the lure connector 74, the clamp 36 is closed until the pump is ready to be used. Priming the pump 20 and tubing 70 eliminates air from the system which may be disadvantageous if introduced to a patient. Moreover, removing air from the system is important to prevent air blocks which may inhibit catheter performance.

Next, a syringe filled with the fluid is connected to the catheter 76 via connector 72 or a catheter hub (not shown). The catheter is then primed until all air has been removed from the catheter.

Once the system has been primed with fluid, the guide needle 78 with introducer tubing 82, 110 is placed within the patient. Preferably, the guide needle 78 is inserted through a pierce site in the skin approximately 3–5 cm away from the wound site and incision site. The introducer needle 78 is then put through the patient's tissue to the wound site W. Next, while holding the introducer tubing 82 in place, the guide needle 78 is safely withdrawn and discarded. Importantly, the needle is discarded prior to introduction of the catheter 76 to the system, thereby eliminating the risk of ripping the catheter or piercing the skin of the healthcare worker.

Next, the catheter 76 is threaded through the introducer catheter 82, 110 to the wound site. Next, the introducer catheter 82, 110 is withdrawn from the puncture site P. As discussed previously, the introducer catheter 110 which may be peeled from the catheter 76 is strongly preferable to the introducer catheter 82 because it may be peeled away from the catheter 76 and the catheter 76 may be integral with a hub or connector 72. Using the introducer catheter 110, many steps in the process are eliminated. For example, if the introducer tubing 82 is used, the healthcare worker would need to first connect the catheter 76 to the connector 72 in order to connect the connector 72 to a syringe to prime the catheter 76. Then, the connector 72 would need to be removed from the catheter 76 to allow the introducer tubing 82 to be slid off of the end of the catheter 76. Thereafter, the catheter 76 would need to be resecured to the connector 72 which would then be connected to the distal end of the tubing 70 by connector 74. By using a split introducer catheter 110, the catheter may be secured to a hub or connector 72 prior to use which will assist healthcare workers in 1) easily priming the catheter 76, and 2) easily placing the catheter 76 in fluid communication with the tubing 70 and pump 20. Thus, use of the split introducer catheter 110 is strongly preferred over use of the catheter introducer 82. Multiple connections and disconnections of the catheter 76 and connector 72 increase the risk of infection to a patient and the risk of improper connections resulting in fluid leaking from the system prior to reaching the wound site W.

Once the catheter has been threaded into the wound site through the introducer catheter 110 and the introducer catheter 110 has been removed and discarded, a syringe is connected to the hub or connector 72 to prime the catheter with fluid anesthetic again. Next, the catheter 76 is placed in fluid communication with the tubing 70 and the clamp 36 is opened to commence infusion.

As will be understood by those of skill in the art, the catheter 76 outside of the body of the patient should be coiled and secured to the patient so as not to kink or pull out of the patient. In addition, it is recommended that the flow restrictor 62 be secured to the skin of the patient. Finally, the pump 20 may be clipped to the patient or placed in a carrying case which a patient may easily carry. Once all of the fluid has traveled from the pump to the wound site, the infusion of anesthetic is complete.

Alternative Catheter Embodiments for Uniform Delivery of Fluid

For use in many of the applications of the above methods, an improved catheter will now be described which provides uniform delivery of fluid medication, and which is effective for both high flow rate and low flow rate fluid delivery.

FIGS. 10–14 illustrate an infusion catheter 320 according to one embodiment of the present invention. Catheter 320 preferably includes a flexible support 322 (FIGS. 12–14), a non-porous membrane 324, and a porous membrane 326. The membranes 324 and 326 are wrapped around the support 322 to form a plurality of axial lumens between the inner surfaces of the membranes 324 and 326 and the surface of the support 322, as described in greater detail below. The non-porous membrane 324 defines a non-infusing section 328 of the catheter 320, and preferably covers the support 322 from the proximal end thereof to a point 330, shown in FIG. 20. Similarly, the porous membrane 326 defines an infusion section 332 of catheter 20, and preferably covers the support 322 from the point 330 to the distal end of support 322. Alternatively, the catheter 320 may be configured without a non-porous membrane 324. In this configuration, the porous membrane 326 covers the entire length of the support 322, so that the entire length of the support 322 corresponds to the infusion section of the catheter 320. The infusion section can have any desired length. The proximal end of the catheter 320 may be connected to a fluid supply 334 containing a fluid 336 such as a liquid medication. The distal end of catheter 320 may include a cap 348 (FIG. 14) defining the endpoint of the axial lumens within the catheter 320.

In use, the catheter 320 is inserted into an anatomical system, such as a human body, to deliver fluid medication directly to a wound area within the anatomical system. In particular, the catheter 320 is designed to deliver medication throughout a generally linear segment of the wound area, corresponding to the infusion section 332 of the catheter 320. Thus, the catheter is preferably inserted so that the infusion section 332 is positioned within the wound area. By using well known methods, a physician or nurse may insert the catheter 320 with the aid of an axial guide wire 346 positioned within an axial guide wire lumen 344 of the catheter. Once the catheter is positioned as desired, the guide wire 346 is simply pulled back out through the proximal end of the catheter 320. Alternatively, the catheter 320 may be provided without a guide wire or a guide wire lumen and inserted using the methods discussed hereinabove.

FIGS. 12 and 13 illustrate a preferred configuration of the support 322. The surface of the support 322 includes interruptions such as a plurality of ribs 340 as shown in the figures. The interruptions are configured so that when the membranes 324 and 326 are wrapped around the support 322, the membranes form a portion of the walls of a plurality of axial lumens 338 within which the fluid 336 may flow. In a preferred configuration, a plurality of ribs 340 extend radially from a common axial center portion 342 of the support 322. The ribs 340 also extend longitudinally along a length of the support 322, and preferably along the entire length thereof. In the non-infusing section 328, shown in FIG. 12, the non-porous membrane 324 is preferably tightly wrapped around the outer edges of the ribs 340. As a result, the axial lumens 338 are formed between the inner surface of the non-porous membrane 324 and the outer surface of support 322. Similarly, in the infusion section 332, shown in FIG. 13, the porous membrane 326 is preferably tightly wrapped around the outer edges of the ribs 340, so that the axial lumens 338 are formed between the inner surface of porous membrane 326 and the outer surface of support 322.

In an alternative embodiment of the catheter 320, the porous membrane 326 may be wrapped around the entire length of the support 320, thus replacing the non-porous membrane 324. In this embodiment, the entire length of the support 322 corresponds to the infusion section 332. According to another alternative embodiment, the support 322 may extend only within the infusion section 332, and a tube may be provided extending from the fluid supply 334 to the proximal end of the support 322. In this embodiment, the tube replaces the non-porous membrane 324 and the portion of the support 322 extending within the non-infusing section 328 of the preferred embodiment. In other words, the tube defines the non-infusing section 328.

In the preferred configuration, the number of ribs 340 equals the number of axial lumens 338. Although five ribs 340 and axial lumens 338 are shown in FIGS. 12 and 13, any suitable number of ribs 340 and lumens 338 may be provided, giving due consideration to the goals of providing a plurality of lumens within the catheter 320, maintaining flexibility, and, if desired, maintaining the fluid independence of the lumens. Herein, the terms "fluid independence," "fluid separation," and the like, when used to describe a plurality of axial lumens, simply mean that the lumens do not fluidly communicate with each other. The membranes 324 and 326 are preferably glued along the outer edges of the ribs 340, utilizing any suitable glue, such as a medical grade glue or epoxy. This prevents the membranes 324 and 326 from slipping, which might occur as the catheter is inserted or removed from the anatomy. More preferably, the membranes are glued along the entire length of the outer edges of each of the ribs 340. Alternatively, the membrane may be wrapped around the support and not secured to the support by a foreign substance. The membrane and support may also be secured to each other by other means known to those of skill in the art. This maintains the fluid independence of the lumens 338. If desired, an axial guide wire lumen 344 may be provided within the axial central portion 342 of the support 322. The guide wire lumen 344 is adapted to receive a guide wire 346 which may be used to aid in the insertion of the catheter 320 into the anatomy, as described above and as will be easily understood by those of skill in the art.

As shown in FIG. 14, the catheter 320 preferably includes an end portion or cap 348 secured to the distal end of support 322. End portion 348 may be formed integrally with the support 322 or may be adhesively bonded thereto. Preferably, the proximal end of end portion 348 is circular and has a diameter such that the outer surface of the proximal end of end portion 348 is aligned with the outer edges of the ribs 340 of the support 322, as shown. The porous membrane 326 is wrapped around the proximal end of the end portion 348. The membrane 326 is preferably glued or secured to the end portion 348 so that fluid 336 within the lumens 338 is prevented from exiting the catheter 320 without passing through the walls of the membrane 326. End portion 348 blocks axial fluid flow through the distal end of catheter 320. However, end portion 348 may optionally be formed from a porous material to permit some axial dispensation of fluid from the distal end of the catheter 320, if desired. The distal end of end portion 348 is preferably dome-shaped, as shown, to permit the catheter 320 to more easily be inserted into an anatomical region.

The support 322 can be formed from a variety of materials, giving due consideration to the goals of flexibility, light-weight, strength, smoothness, and non-reactivity to anatomical systems, i.e., safety. Suitable materials for the support 322 include nylon, polyamide, Teflon, and other materials known to those skilled in the art. The porous membrane 326 is preferably a sponge-like or foam-like material or a hollow fiber. The membrane 326 may be formed from a variety of suitable materials, giving due consideration to the goals of being flexible and non-reactive to anatomical systems. The membrane 326 preferably has a porosity resulting in substantially uniform dispensation of fluid along the surface area of the infusion section 332 of the catheter 320, and has an average pore size sufficiently small to limit the flow of bacteria through the membrane walls. Some suitable materials for the membrane 326 are polyethylene, polysulfone, polyethersulfone, polypropylene, polyvinylidene difluoride, polycarbonate, nylon, or high density polyethylene. These materials are advantageously biocompatible. The porous membrane 326 may filter out unwanted bacteria from the fluid medication as it passes through the membrane 326. It is known that the smallest bacteria cannot pass through a pore any smaller than 0.23 microns. Thus, the average pore size, or pore diameter, of the porous membrane 326 may be less than 0.23 microns to prevent bacteria from traversing the membrane 326. The average pore size, or pore diameter, of the membrane 326 is preferably within the range of about 0.1 to 1.2 microns, more preferably within the range of about 0.3 to 1 micron, and even more preferably about 0.45 microns.

As mentioned above, the proximal end of catheter 320 may be connected to a fluid supply 334. The catheter 320 may be configured so that each axial lumen 338 is fluidly independent. In other words, the lumens 338 would not fluidly communicate with one another. The catheter 320 may be connected to a single fluid supply 334, so that the fluid 336 flows within each of the lumens 338. Alternatively, the catheter 320 may be connected to a plurality of separate fluid supplies so that several different fluids may separately flow within the lumens 338. According to this configuration, each lumen 338 may be connected to a separate fluid supply so that the total number of different fluids that may be delivered to the anatomy is equal to the number of lumens 338. Alternatively, the fluid lumens need not be fluidly independent. For example, the membrane 326 may not be secured to the support 322 along the entire length of the support 322, thus permitting fluid 336 to migrate between lumens 338.

In operation, the catheter 320 delivers fluid directly to the area of the anatomy that is adjacent to the infusion section 332. The fluid 336 from the fluid source 334 is introduced into the axial lumens 338 at the proximal end of the catheter 320. The fluid 336 initially flows through the non-infusing section 328. When the fluid 336 first reaches the infusion section 332, it soaks into the porous membrane 326. As more fluid 336 enters the infusion section 332, it diffuses longitudinally within the walls of the membrane 326 until the entire membrane 326 and infusion section 332 are saturated with fluid. At this point the fluid 336 begins to pass through the membrane 326, thereby exiting the catheter 320 and entering the anatomy. Moreover, the fluid 336 advantageously passes through the entire surface area of the porous membrane 326 at a substantially uniform rate, due to the characteristics of the membrane 326. Thus, the fluid is delivered at a substantially equal rate throughout a generally linear segment of the wound area of the anatomy. Furthermore, this advantage is obtained for both low and high pressure fluid delivery.

FIGS. 15 and 16 illustrate a catheter 350 according to an alternative embodiment of the present invention. According to this embodiment, the catheter 350 includes an elongated outer tube 352 and an inner elongated tubular porous membrane 354. The tubular membrane 354 is preferably concentrically enclosed within the outer tube 352. More preferably, the tube 352 tightly surrounds and supports the tubular membrane 354 so that a relatively tight fit is achieved between the inner dimensions of tube 352 and the outer dimensions of membrane 354. A plurality of fluid exit holes 356 are provided within the tube 352, preferably throughout the entire circumference thereof. The portion of tube 352 that includes the exit holes 356 defines the infusion section of catheter 350. The tubular membrane 354 need only be provided along the length of the infusion section, but could be longer. Optionally, axial exit holes may be provided within the distal tip 358 of the tube 352. Also, a guide wire and/or guide wire lumen may be provided to aid in the insertion of the catheter 350 into the anatomy, as will be understood by those skilled in the art. Alternatively, any of the catheters disclosed herein may be introduced to a wound site using the methods discussed herein (i.e., via an introducer catheter 82, 110).

The tube 352 may be formed from any of a variety of suitable materials, such as nylon, polyamide, Teflon and other materials known to those skilled in the art, giving due consideration to the goals of non-reactivity to anatomical systems, flexibility, light-weight, strength, smoothness, and safety. In a preferred configuration, the tube 352 is preferably a 20 gauge catheter tube, having inside and outside diameters of 0.019 inches and 0.031 inches, respectively. The exit holes 356 of tube 352 are preferably about 0.015 inches in diameter and provided at equally spaced axial positions along the tube 352. The holes 356 are preferably arranged so that every hole is angularly displaced about 120° relative to the longitudinal axis of the tube 352, from the angular location of the previous hole. The axial separation between adjacent exit holes 356 is preferably within the range of about 0.125 to 0.25 inches, and more preferably about 3/16 inch. Also, the infusion section can have any desirable length. This configuration results in a thorough, uniform delivery of fluid throughout a generally linear segment of the wound area. Of course, the exit holes 356 may be provided in any of a variety of alternative arrangements.

The tubular porous membrane 354 is preferably a sponge-like or foam-like material or a hollow fiber. The tubular membrane 354 may have an average pore size, or pore diameter, less than 0.23 microns to filter bacteria. The pore diameter is preferably within the range of about 0.1 to 1.2 microns, more preferably within the range of about 0.3 to 1 micron, and even more preferably about 0.8 microns. The tubular membrane 354 may be formed from any of a variety of suitable materials, giving due consideration to the goals of non-reactivity to anatomical systems, maintaining flexibility, fitting within the size constraints of the tube 352, and having a porosity resulting in the substantially uniform dispensation of fluid through all of the exit holes 356 in tube 352. Some suitable materials for the membrane 354 are polyethylene, polysulfone, polyethersulfone, polypropylene, polyvinylidene difluoride, polycarbonate, nylon, or high density polyethylene. Preferable inside and outside diameters of the tubular membrane 354 are 0.010 inches and 0.018 inches, respectively. In the event that a guide wire 346 is provided, the guide wire may be a stainless steel wire about 0.005 inches in diameter. The tube 352 may be secured to the membrane 354 by epoxy or other means known to those skilled in the art. Alternatively, the membrane 354 may contact the tube 352 with an interference fit and not use other materials to secure the membrane 354 in the tube 352.

In operation, the catheter 350 delivers fluid to the region of an anatomical system adjacent to the infusion section of catheter 350. As the fluid flows into the infusion section, it initially soaks into the tubular porous membrane 354. As more fluid enters the infusion section, the fluid diffuses longitudinally within the walls of the tubular member 354. Once the membrane 354 and the tubular space therein are saturated, the fluid passes through the membrane 354 and exits the catheter 350 by flowing through the exit holes 356 of the tube 352. Moreover, the fluid advantageously passes through the membrane substantially uniformly throughout the surface area of the membrane 354, resulting in a substantially uniform flow through substantially all of the exit holes 356. Thus, the fluid is delivered at a substantially equal rate throughout the wound area of the anatomy. Furthermore, this advantage is obtained for both low and high pressure fluid delivery.

FIG. 17 illustrates a catheter 370 according to another embodiment of the present invention. Catheter 370 includes a tube 372 having a plurality of exit holes 376 in side walls of the tube, and a tubular porous membrane 374 concentrically enclosing the tube 372. Catheter 370 operates in a similar manner to catheter 350 described above in connection with FIGS. 15 and 16. In use, fluid medication passes through the exit holes 376 and then begins to soak into the porous membrane 374. The fluid diffuses longitudinally within the walls of the membrane until the membrane is saturated. Thereafter, the fluid leaves the membrane walls and enters the anatomy. Advantageously, the fluid is dispensed to the anatomy at a substantially uniform rate throughout the surface area of the membrane 374. As in the previous embodiments, this advantage is obtained for both low and high pressure fluid delivery.

FIG. 18A illustrates a catheter 360 according to another embodiment of the present invention. Catheter 360 is better suited for relatively high flow rate delivery of fluid to a region within an anatomical system. Catheter 360 includes a tube 362 having a plurality of exit holes 364 of increasing size. In particular, the more distal exit holes are larger in diameter than the more proximal exit holes. The position of the exit holes 364 on the tube 362 defines the length of the infusion section of the catheter 360. The infusion section can have any desired length. The proximal end of catheter 360 is connected to a fluid supply, and a guide wire and/or guide wire lumen may also be provided for aiding in the insertion of catheter 360 into the anatomy.

As discussed above, for high or low pressure fluid delivery, exit holes nearer to the distal end of a catheter tube generally have increased flow resistance compared to exit holes nearer to the proximal end of the tube. Also, the fluid flowing through the more distal holes experiences a greater pressure drop. Consequently, there is generally a greater flow rate of fluid through the more proximal holes, resulting in non-uniform fluid delivery. In contrast, catheter 360 advantageously provides substantially uniform fluid delivery through substantially all of the exit holes 364, under relatively high flow rate conditions. This is because the larger size of the more distal holes compensates for their increased flow resistance and pressure drop. In other words, since the more distal holes are larger than the more proximal holes, there is a greater flow rate through the more distal holes than there would be if they were the same size as the more proximal holes. Advantageously, the holes 364 are provided in a gradually increasing size which results in substantially uniform fluid delivery. In addition, the exit holes 364 may be sized so that they combine to form a flow-restricting orifice, as described below in connection with the embodiment of FIG. 22.

As compared to prior art catheters, catheter 360 is advantageously simple and easy to manufacture. All that is required is to drill a plurality of exit holes 364 in the tube 362. Furthermore, catheter 360 can sustain greater bending than prior art catheters while maintaining operability. In contrast to prior art catheters, such as the Wang catheter, if the tube 362 is bent somewhat, it will still deliver fluid relatively uniformly. This is because the tube 362 has a single lumen with a relatively large cross-section. When the tube 362 is somewhat bent, fluid flowing within the lumen is less likely to experience blockage and a consequent pressure change which might lead to non-uniform fluid dispensation.

The tube 362 of catheter 360 may be formed from any of a wide variety of materials, giving due consideration to the goals of non-reactivity to anatomical systems, flexibility, light-weight, strength, smoothness, and safety. Suitable materials include nylon, polyamide, Teflon, and other materials known to those skilled in the art. The infusion section can have any desired length but is preferably about 0.5 to 20 inches long, and more preferably about 10 inches long. The diameter of the exit holes 64 preferably ranges from about 0.0002 inches at the proximal end of the infusion section to about 0.01 inches at the distal end thereof. The largest, i.e., most distal, exit hole 364 is preferably about 0.25 inches from the distal end of the tube 362. In the preferred configuration, the axial separation between adjacent holes 364 is within the range of about 0.125 to 0.25 inches, and more preferably about 3/16 inch. Optionally, the holes 364 may be provided so that adjacent holes are angularly displaced by about 120° as in the embodiment of FIG. 15. Of course, if too many exit holes 364 are provided, the tube 362 may be undesirably weakened.

FIG. 18B illustrates yet another embodiment of the catheter of the present invention. In this embodiment, catheter 370 includes multiple exit holes 371, 372. The longitudinal distance between proximal exit holes 371 is larger than the longitudinal distance between exit holes 372. By increasing the distance between holes at the proximal end of the infusion portion of the catheter 370, and decreasing the distance between exit holes 372 at the distal end of the infusion section of the catheter 370, a more even flow of fluid throughout the infusion section of the catheter will be achieved, especially at higher pressures as will be understood by those of skill in the art.

Another catheter of the present invention is illustrated in FIG. 18C. This catheter 374 includes a plurality of holes 375–379 along the length of the catheter. The distance between the first exit hole 375 and second exit hole 376 is larger than the distance between the second exit hole 376 and the third exit hole 377. Likewise, the distance between exit holes 376 and 377 is larger than the distance between exit holes 377 and 378 in the longitudinal direction along the catheter. Similarly, the distance between exit holes 377 and 378 is larger than the distance between exit holes 378 and 379. Thus, by continually decreasing the distance between exit holes while traveling distally along the length of the catheter, a more even flow rate of fluid through the catheter is achieved, especially at high pressures.

Of course, it is contemplated by the present inventors that one may provide larger or smaller exit holes or adjust the various distances between various exit holes and still achieve the results of the present invention. Thus, any such modifications are considered within the scope of the present invention.

Figure 19:
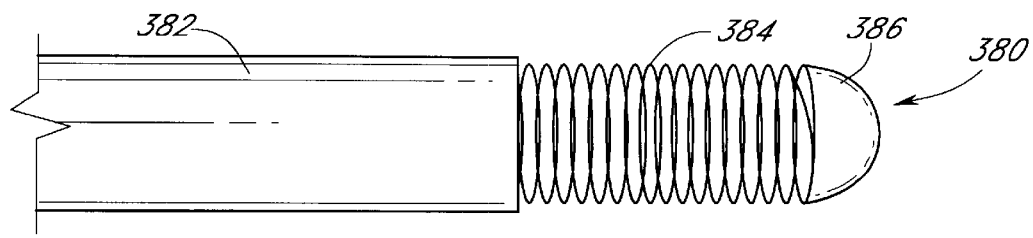
FIG. 19 is a side view of a catheter having features and advantages in accordance with another embodiment of the present invention.
Figure 20A:
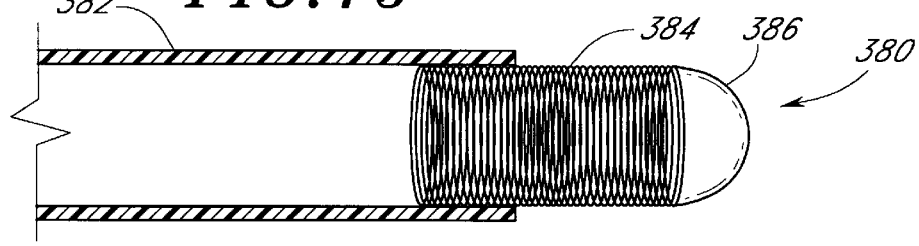
FIG. 20A is a cross-sectional view of the catheter of FIG. 19, illustrating an unstretched state of the spring.
Figure 20B:
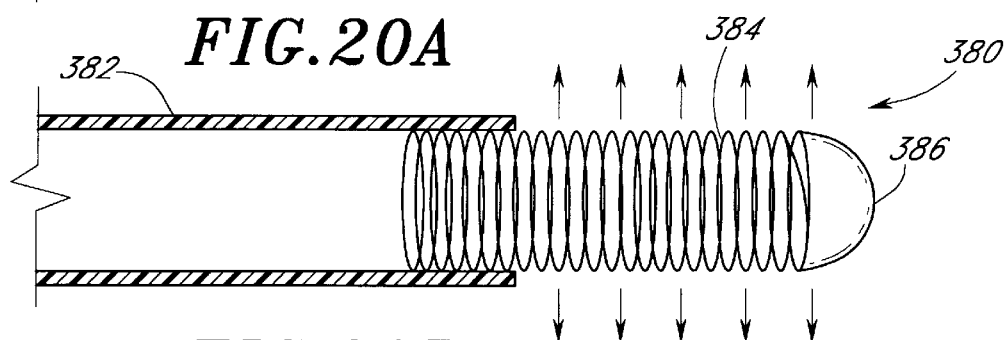
FIG. 20B is a cross-sectional view of the catheter of FIG. 19, illustrating a stretched state of the spring.

FIGS. 19, 20A, and 20B illustrate a catheter 380 according to another embodiment of the present invention. The catheter 380 comprises a tube 382, a "weeping" tubular coil spring 384, and a stop 386. The proximal end of the spring 384 is attached to the distal end of the tube 382 so that the tube and spring each define a portion of a central lumen. A preferably dome-shaped stop 386 is attached to and closes the distal end of the spring 384. The portion of the spring 384 that is distal to the tube 382 comprises the infusion section of the catheter 380. In an unstretched state, shown in FIG. 20A, the spring 384 has adjacent coils in contact with one another so that fluid within the spring and below a threshold dispensation pressure is prevented from exiting the lumen by flowing radially between the coils. The spring 384 has the property of stretching longitudinally, as shown in FIG. 20B, when the fluid pressure is greater than or equal to the threshold dispensation pressure of the spring, thereby permitting the fluid to be dispensed from the lumen by "weeping," i.e., leaking radially outward between the coils. Alternatively, the spring may stretch radially without elongating to permit fluid to weep through the coils of the spring. Further, the spring may stretch both longitudinally and radially to permit weeping, as will be understood by those of skill in the art. Advantageously, the fluid between the coils of the spring is dispensed substantially uniformly throughout the length and circumference of the portion of the spring that is distal to the tube 382, i.e., the infusion section. The catheter 380 can be used for both high or low flow rate fluid delivery.

In use, the catheter 380 is inserted into an anatomical region so that the spring 384 is in a region to which fluid medication is desired to be delivered. The spring is initially in an unstretched state, as shown in FIG. 20A. The fluid is introduced into a proximal end of the tube 382 of the catheter 380 and flows into and through the spring 384 until it reaches the stop 386. As fluid is continually introduced into the proximal end of the tube 382, the fluid builds inside of the spring 384. When the spring 384 is filled with fluid, the fluid pressure rises more quickly. The fluid imparts a force directed radially outward onto the spring coils. As the pressure builds, the outward force becomes larger. Once the fluid pressure rises to the threshold dispensation pressure, the outward force causes the spring coils to separate slightly so that the spring stretches longitudinally, as shown in FIG. 20B. Alternatively, the coils may separate radially, as discussed above. The fluid then flows through the separated coils to be dispensed from the catheter 380. Moreover, the dispensation is advantageously uniform throughout the infusion section of the catheter 380. As fluid is continually introduced into the tube 382, the spring 384 remains stretched to continually dispense fluid to the desired region within the anatomy. If the fluid introduction temporarily ceases, the fluid pressure within the spring 384 may fall below the threshold dispensation pressure. If so, the spring will compress so that the coils are once again adjacent and the fluid is no longer dispensed.

Several spring types will achieve the purposes of this invention. Suitable spring types are 316L or 402L, which can be readily purchased. In a preferred configuration, the spring 384 has about 200 coils per inch along its length. In this configuration, the spring can advantageously sustain a high degree of bending without leaking fluid from within, and only a severe bend will cause adjacent coils to separate. Thus, the spring 384 may be flexed considerably within an anatomical region without causing fluid to leak and therefore be dispensed to only one region within the anatomy. The spring 384 can have any desired length to define the length of the infusion section of the catheter 380. The spring may be formed from a variety of materials, giving due consideration to the goals of strength, flexibility, and safety. A preferred material is stainless steel. In the preferred configuration, the inside and outside diameters of the spring are about 0.02 inches and 0.03 inches, respectively, and the spring wire has a diameter of about 0.005 inches. The proximal end of the spring 384 is preferably concentrically enclosed within the distal end of the tube 382. The spring can be glued to the inside wall of the tube 382 using, for example, a U.V. adhesive, a potting material, or other bonding materials. Alternatively, the spring can be soldered within the tube 382 or be fitted with a proximal plug and tightly plugged into the tube 382.

The tube 382 and stop 386 can be formed from any of a variety of materials, giving due consideration to the goals of flexibility, light-weight, strength, smoothness, and safety. Suitable materials include nylon, polyamide, Teflon, and other materials known to those skilled in the art.

Figure 21:
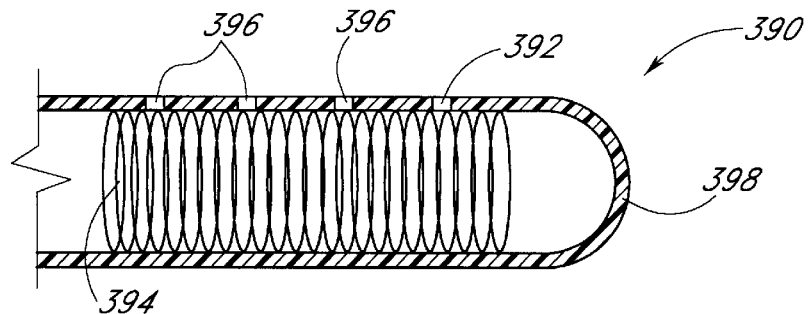
FIG. 21 is a cross-sectional view of a catheter having features and advantages in accordance with another embodiment of the present invention.

FIG. 21 illustrates a catheter 390 according to another embodiment of the present invention. The catheter 390 comprises a distally closed tube 392 and a "weeping" tubular coil spring 394 concentrically enclosed within the tube 392 so that a lumen is defined within the tube and spring. A plurality of exit holes 396 are provided along a length of the tube 392, in the side wall thereof. The length of the tube 392 including such exit holes 396 defines an infusion section of the catheter 390. The exit holes 396 are preferably provided throughout the walls of the infusion section. The infusion section can have any desired length. In the preferred configuration, the axial spacing between adjacent holes 396 is within the range of about 0.125 to 0.25 inches, and more preferably about 3/16, inch. Adjacent holes 396 are preferably angularly spaced apart by about 120°. The spring 394 is preferably enclosed within the infusion section of the catheter and configured similarly to the spring 384 of the embodiment of FIGS. 19, 20A and 20B. The spring 394 is preferably longer than the infusion portion and positioned so that all of the exit holes 396 are adjacent to the spring 394. In this configuration, the fluid is prevented from exiting the lumen without flowing between the spring coils. A stop is preferably attached to the tube to close the distal end thereof. Alternatively, the tube 392 may be formed with a closed distal end. The catheter 390 can be used for high or low flow rate fluid delivery.

In use, the catheter 390 is inserted into an anatomical region so that the infusion section is in a region to which fluid medication is desired to be delivered. The fluid is introduced into a proximal end of the tube 392 of the catheter 390 and flows through the spring 394 until it reaches the closed distal end of the tube 392. As fluid is continually introduced into the proximal end of the tube 392, the fluid builds inside of the spring 394. Eventually, the spring 394 becomes filled with fluid, the fluid pressure rises, and the fluid weeps through the spring coils as described above in connection with the embodiment of FIGS. 19, 20A, and 20B. Moreover, the fluid flows through the spring coils substantially uniformly throughout the length and circumference of the spring 394. The fluid then exits the tube 392 by flowing through the exit holes 396 of the infusion section. The exit holes are preferably equal in size so that the fluid flows at a substantially equal rate through the exit holes, advantageously resulting in a generally uniform distribution of fluid throughout a desired region of the anatomy. As fluid is continually introduced into the catheter 390, the spring 394 remains stretched to continually dispense fluid from the catheter. If the fluid introduction ceases temporarily, the fluid pressure within the spring 394 may fall below the threshold dispensation pressure. If so, the spring may compress so that the coils are once again adjacent and the fluid is no longer dispensed.

In the preferred configuration, the spring 394 and tube 392 are in contact along the entire length of the spring, so that the fluid weeping through the spring is forced to flow through the holes 396 of the infusion section. Preferably, one end of the spring 394 is attached to the inside walls of the tube 392, permitting the other end of the spring to be displaced as the spring stretches. The spring can be glued to the tube 392 with, for example, a U.V. adhesive, potting material, or other bonding materials. Alternatively, an end of the spring can be soldered onto the inner walls of the tube 392. The tube 392 can be formed from any suitable material. The inside walls of the tube 392 are preferably smooth so that the spring can more freely stretch and compress.

Figure 22:
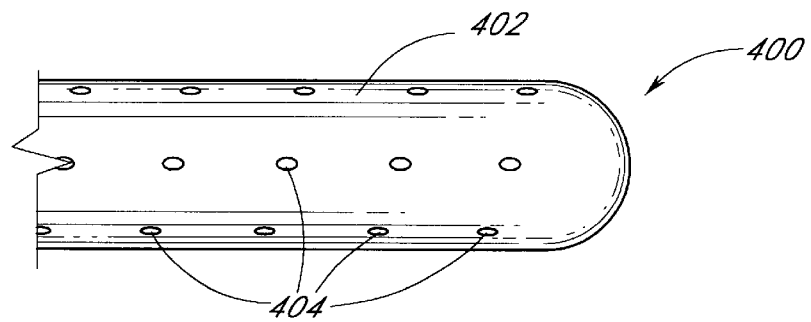
FIG. 22 is a side view of a catheter having features and advantages in accordance with the embodiment of FIG. 21.

FIG. 22 illustrates a catheter 400 according to another embodiment of the present invention. The catheter 400 comprises a distally closed tube 402 having a plurality of exit holes 404 in side walls of the tube 402. The portion of the tube 402 having exit holes 404 defines an infusion section of the catheter 400. The exit holes 404 are sized to have a combined area of opening that is smaller than the area of any other flow-restricting cross-section or orifice of the catheter. Thus, the exit holes 404 are the flow-restrictor of the catheter 400. In use, the catheter advantageously dispenses fluid through substantially all of the exit holes 404. A fluid introduced into a proximal end of the tube 402 flows through the tube until it reaches the closed distal end thereof. At this point, the fluid builds within the infusion portion of the catheter. The fluid is substantially prevented from flowing through the holes 404, due to their small size. Eventually, the infusion portion of the catheter becomes filled with fluid. As fluid is continually introduced into the proximal end of the tube 402, the fluid pressure begins to build. At some point the pressure becomes sufficiently high to force the fluid through the exit holes 404. Moreover, the fluid flows through substantially all of the exit holes 404.

In this preferred configuration, the exit holes 404 are all equal in size so that the fluid is dispensed at a substantially equal rate through substantially all of the holes. The holes 404 are preferably laser drilled to achieve a very small hole diameter. A preferred diameter of the exit holes 404 is about 0.0002 inches, or about 5 microns. Numerous exit holes 404 may be provided within the tube 402. The holes are advantageously provided throughout the circumference of the infusion portion of the catheter 400, to more uniformly deliver the fluid throughout an anatomical region. A preferred axial spacing between adjacent holes 404 is within the range of about 0.125 to 0.25 inches, and more preferably about 3/16 inch. The catheter 400 can be used for high or low flow rate fluid delivery. The tube 402 can be formed from any of a variety of materials known to those skilled in the art and discussed previously.

Figure 23:
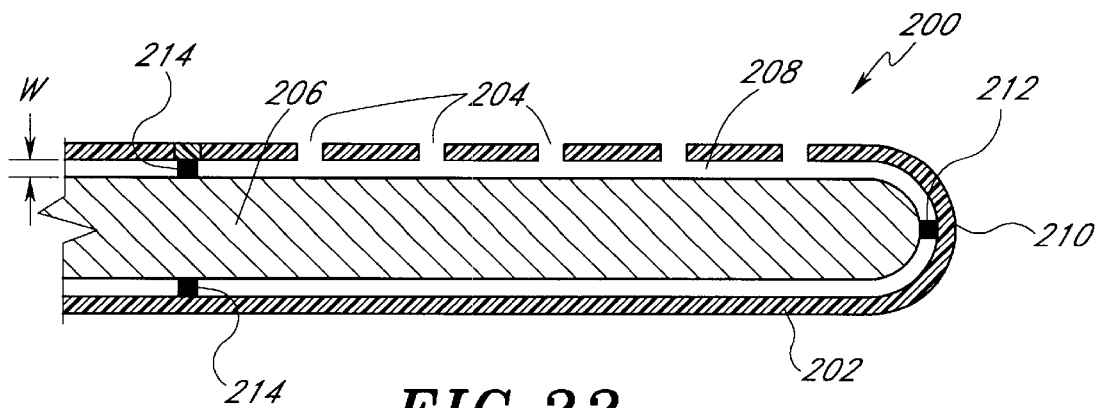
FIG. 23 is a longitudinal cross-sectional view of a catheter having features and advantages in accordance with another embodiment of the present invention.

FIG. 23 illustrates a catheter 200 according to another embodiment of the present invention. Catheter 200 includes a distally closed tube 202 having a plurality of exit holes 204 therein along an infusion section of the catheter, as in the above-described embodiments. The holes 204 are desirably provided throughout the circumference of the tube 202. Enclosed within the tube 202 is an elongated member 206 formed of a porous material. Preferably, the member 206 is generally cylindrical in shape, and solid. Preferably, the member 206 is positioned within the tube 204 so that an annular space 208 is formed between the outer surface of the member 206 and the inner surface of the tube 202. Preferably, the member 206 extends from the distal end 210 of the tube 202 rearwardly to a point proximal of the infusion section of the catheter. Alternatively, the member 206 may extend along only a portion of the infusion section. The member 206 is preferably generally concentric with the tube 202, but non-concentric designs will achieve the advantages of the invention. Preferably, the member 206 is manufactured of a flexible material to assist with the placement of the catheter 200 in the body of a patient.

In operation, fluid medication flowing in the tube 202 saturates the porous member 206 and flows into the annular region 208. Once the member 206 is saturated, the fluid in the member 206 flows into the region 208 and out of the catheter 200 through the exit holes 204. Advantageously, since the fluid pressure is uniform throughout the annular region 208, the fluid flows substantially uniformly through all of the holes 204. There are several advantages of the annular region 208. One advantage is that it tends to optimize the uniformity of flow through the exit holes 204. Also, the member 206 may be formed from a porous material that tends to expand when saturated with liquid. If so, the member 206 preferably expands into the annular region 208 without pressing against the tube 202. This limits the possibility of high pressure regions at the interior surface of the tube 202, which could cause uneven exit flow of the medication within the wound site. Alternatively, the member 206 may expand and come into contact with the tube 202, and still accomplish the goals of the present invention.

The member 206 is formed of a porous material having an average pore size preferably within the range of 0.1–50 microns, and more preferably about 0.45 microns. The radial width W of the annular region 208 is preferably within the range of 0 to about 0.005 microns, and more preferably about 0.003 microns. The member 206 can be formed of any of a variety of materials, giving due consideration to the goals of porosity, flexibility, strength, and durability. A preferred material is Mentek.

Figure 24:
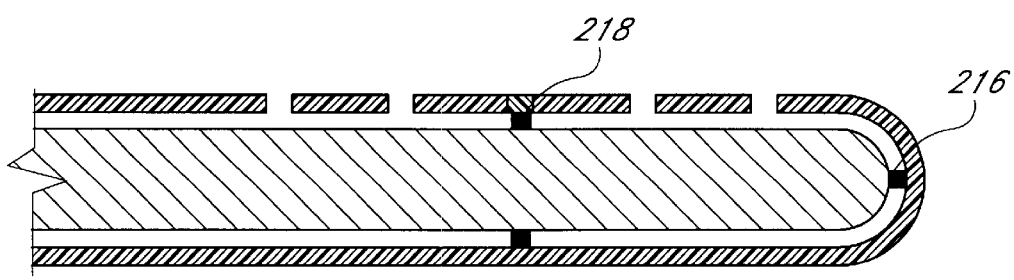
FIGS. 24–26 are longitudinal cross-sectional views of catheters similar to that of FIG. 23, illustrating alternative attachments between the internal porous member and the tube.
Figure 25:
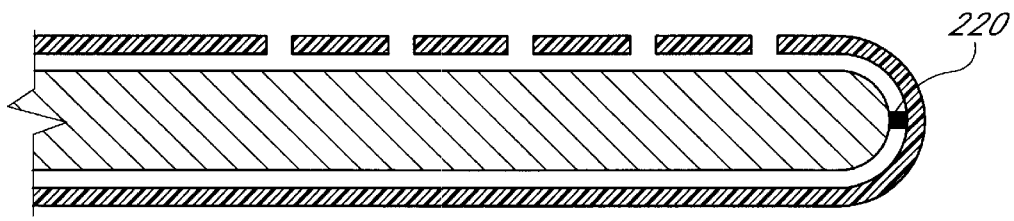
Figure 26:
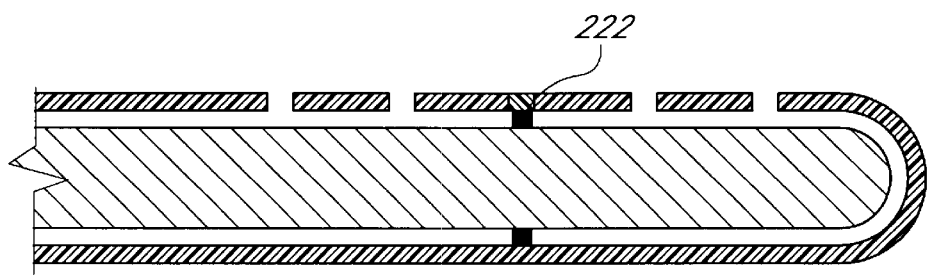

The member 206 can be secured within the tube 202 by the use of an adhesive. In one embodiment, as shown in FIG. 23, the adhesive is applied at the distal end of the member 206 to form a bond with the interior surface of the distal end of the tube 202. Preferably, adhesive is applied at or near the proximal end of the infusion section of the catheter 200. Additionally, the adhesive can be applied to the circumference of the member 206 at any longitudinal position thereof, forming a ring-shaped bond with the interior surface of the tube 202. For example, in the embodiment of FIG. 23, a ring-shaped bond 214 is provided just proximal of the infusion section of the catheter 200. Other configurations are possible. For example, FIG. 24 shows an embodiment in which the adhesive is applied to the distal end of the member 206 to form a bond 216, and also at generally the center of the infusion section to form a ring-shaped bond 218. FIG. 25 shows an embodiment in which the adhesive is applied only to the distal end of the member 206 to form a bond 220. FIG. 26 shows an embodiment in which the adhesive is applied only to the center of the infusion section to form a ring-shaped bond 222. Those of ordinary skill in the art will understand from the teachings herein that the adhesive may be applied in any of a variety of configurations. Thus, for example, adhesive at the distal end of the catheter (i.e., 212, 216, and 220 in FIGS. 23, 24, and 25, respectively) is not required.

In the current best mode of the invention, preferably two bonds are incorporated one at the most proximal hole and one at the most distal hole of the catheter. Each bond is formed with an adhesive as described below.

The ring-shaped bond 214 can be formed by pouring the adhesive in liquid form through one of the exit holes 204 when the member 206 is in the tube 202. The adhesive, having a generally high viscosity, tends to flow about the circumference of the member 206, rather than into the body of the member. The adhesive thus forms a ring-shaped bond with the tube 202, as will be understood by those of skill in the art. Also, the adhesive plugs the exit hole 204 through which it is poured. Any of a variety of different types of adhesives will be acceptable, a preferred adhesive being Loctite.

Figure 27:
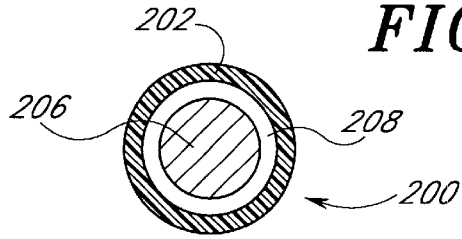
FIG. 27 is a transverse cross-sectional view of a catheter according to FIGS. 23–26, wherein the internal porous member is concentric with the outer tube.
Figure 28:
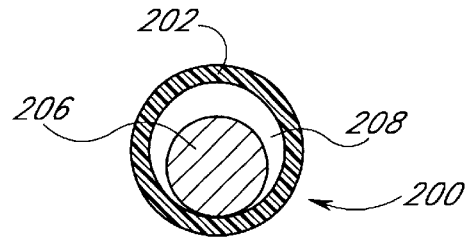
FIG. 28 is a transverse cross-sectional view of a catheter according to FIGS. 23–26, wherein the internal porous member is not concentric with the outer tube.
Figure 29:
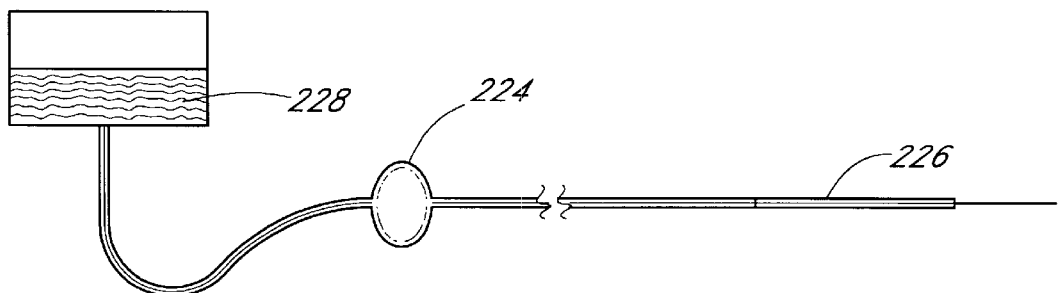
FIG. 29 is a schematic illustration of a catheter of the present invention used in conjunction with an air eliminating filter.

As mentioned above, the member 206 is preferably concentric with the tube 202. FIG. 27 shows a cross-section of a catheter 200 in which the member 206 is concentrically enclosed within the tube 202. Alternatively, the member 206 may be positioned adjacent to the tube 202, as shown in FIG. 28. The configuration of FIG. 28 may be easier to manufacture than that of FIG. 27, since the member 206 does not have to be centered within the tube 202.

Those of ordinary skill in the art will understand from the teachings herein that the member 206 can be of any desired length and can extend along any desired length of the infusion section of the catheter 200. For example, the member 206 does not have to extend to the distal end of the tube 202. Further, the proximal end of the member 206 may be either distal or proximal to the proximal end of the infusion section.

When any of the catheters of the above embodiments is used, the catheter may initially have air inside of the catheter tube. For example, the catheter 200 shown in FIG. 23 may have air inside of the porous material of the member 206. The introduction of liquid medication into the catheter forces the air to flow out of the exit holes. However, this may take several hours. If the catheter is inserted into a patient while air is inside, and liquid medication is introduced into the catheter, the patient's wound site may receive little or no medication until air is expelled from the catheter tube. Thus, it is preferred to run the liquid medication through the catheter prior to inserting the catheter into a patient, to ensure that the air is expelled from the catheter prior to use. Further, with reference to FIG. 29, an air filter 224, as known in the art, can be inserted into the catheter tubing proximal the infusion section 226 of the catheter 200. The filter 224 prevents undesirable air from entering the infusion section 226 of the catheter 200.

Figure 30:
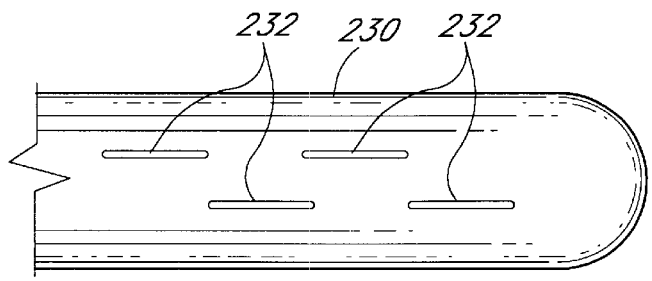
FIG. 30 is a side view of a catheter having features and advantages in accordance with another embodiment of the present invention.
Figure 31:
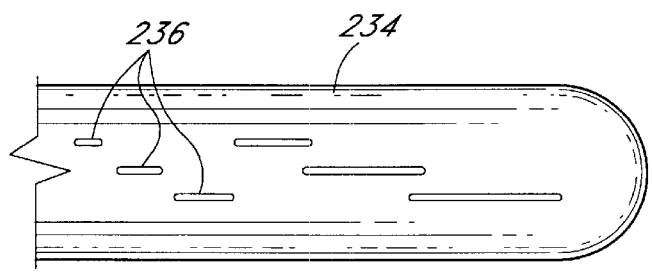
FIG. 31 is a side view of a catheter having features and advantages in accordance with another embodiment of the present invention.

FIGS. 30 and 31 illustrate catheter tubes having elongated exit holes or slots. These catheter tubes may be used in place of the catheter tubes shown and described above. FIG. 30 shows a tube 230 having exit holes or slots 232 that are elongated in the longitudinal direction of the tube 230. The slots 232 are preferably provided throughout the circumference of the tube 230, along the infusion section of the catheter. Compared to smaller exit holes, the elongated slots 232 tend to increase the flowrate of fluid exiting the catheter, by reducing the flow impedance experienced by the fluid. Preferably, the slots 232 may be oriented longitudinally on the catheter body so as not to compromise the structural integrity of the catheter 200, as will be easily understood by those of skill in the art.

FIG. 31 shows a tube 234 having exit holes or slots 236 whose lengths increase along the length of the tube in the distal direction. In the illustrated embodiment, the slots nearer to the proximal end of the infusion section of the tube 234 are shorter in length than the slots nearer to the distal end of the infusion section. As in the embodiment of FIG. 18, the catheter tube 234 advantageously provides substantially uniform fluid delivery through substantially all of the exit slots 236, under relatively high flow rate conditions. This is because the larger size of the more distal slots compensates for their increased flow resistance and pressure drop. In other words, since the more distal slots are larger than the more proximal slots, there is a greater flow rate through the more distal slots than there would be if they were the same size as the more proximal slots. Advantageously, the slots 236 are provided in a gradually increasing length, which results in substantially uniform fluid delivery. Further, the elongated slots result in generally higher exit flowrates, as in the embodiment of FIG. 30.

With regard to all of the above embodiments of catheters, an independent guide wire lumen may be provided within or adjacent to the lumen(s) disclosed, as will be understood by those skilled in the art.

Figure 32:
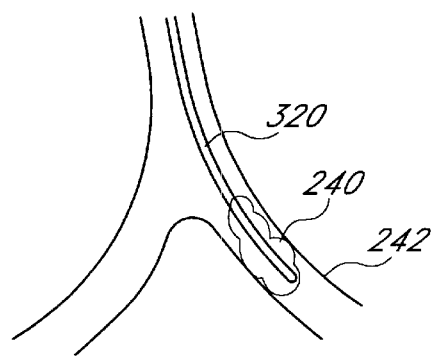
FIG. 32 is a schematic illustration of the use of a catheter of the present invention for treating a blood clot.

The catheters of the present invention can be used in various medical applications. With reference to FIG. 32, in one exemplary application a catheter 120 (reference numeral 120 is used to identify the catheter, but any of the above-described catheters can be used) is inserted into a blood clot 240 inside of a vein or artery 242. Preferably, the infusion section of the catheter is within the blood clot 240. Liquid medication is preferably introduced into the proximal end of the catheter tube. Advantageously, the medication exits the catheter 120 at a uniform rate throughout the infusion section to dissolve the clot 240.

As will be easily understood by those of skill in the art, any of the catheter embodiments described herein may be used in a variety of applications including, but not limited to, peripheral nerve blocks, intrathecal infusions, epidural infusions, intravascular infusions, intraarterial infusions and intraarticular infusions, as well as in wound site pain management.

In addition, any of the catheters disclosed herein may be integral with a fluid line emanating from an infusion pump as opposed to being an independent catheter designed to be connected or secured to an infusion pump.

Moreover, any of the catheters disclosed herein may be introduced to a wound site through the use of an introducer catheter 82, 110 as described in detail above. Thus, any of the catheters discussed herein may be used with the methods of providing anesthetic directly to a wound site to provide pain management.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method of introducing fluid to a wound site of a patient, comprising the steps of:

providing a guide needle within an introducer conduit;

piercing the skin of the patient with the guide needle;

advancing the guide needle through the patient's tissue to a wound site;

removing the guide needle from within the introducer conduit, while leaving a distal end of the introducer conduit in the wound site;

threading an infusion catheter through the introducer conduit, the catheter defining an infusion section and comprising a tube, a tubular coil spring having an end attached to the tube and a stop closing a distal end of the catheter, the spring extending along the infusion section of the catheter and having adjacent coils in contact with one another when the spring is in a relaxed state such that fluid within the spring and below a threshold dispensation pressure is prevented from exiting the catheter by flowing radially between the coils, the spring having the property of stretching when the fluid pressure is greater than or equal to the threshold dispensation pressure and permitting the fluid to be dispensed from the infusion section of the catheter by flowing radially between the coils;

removing the introducer conduit from the patient while leaving the infusion conduit in place in the wound site of the patient;

introducing fluid to the wound site through the infusion catheter.

2. The method of claim 1, wherein the infusion catheter is placed in fluid communication with a pump to infuse the fluid to the wound site.

3. The method of claim 2, wherein the infusion catheter is placed in fluid communication with tubing which is placed in fluid communication with the pump to infuse the fluid to the wound site.

4. The method of claim 3, wherein the pump and a first end of the tubing are bonded together, and a second end of the tubing and the catheter are bonded together.

5. The method of claim 1, wherein the infusion catheter is primed with the fluid.

6. The method of claim 1, wherein the fluid is pain medication.

7. The method of claim 1, wherein the pierce site is approximately 3–5 cm away from the wound site.

8. The method of claim 1, wherein the guide needle is hollow.

9. The method of claim 1, wherein the guide needle has no lumen therethrough.

10. A method of introducing fluid to a wound site of a patient, comprising the steps of:

providing a guide needle within an introducer conduit;

piercing the skin of the patient with the guide needle;

advancing the guide needle through the patient's tissue to a wound site;

removing the guide needle from within the introducer conduit, while leaving a distal end of the introducer conduit in the wound site;

threading a catheter, wherein the catheter comprises an elongated tube having a plurality of exit holes along the length thereof and a tubular porous membrane concentrically enclosed within said tube, through the introducer conduit;

removing the introducer conduit from the patient while leaving the infusion catheter in place in the wound site of the patient;

introducing fluid to the wound site through the infusion catheter; and wherein the average pore diameter of the tubular porous membrane is less than 0.23 micron.

11. A method of introducing fluid to a wound site of a patient, comprising the steps of:

providing a guide needle within an introducer conduit;

piercing the skin of the patient with the guide needle;

advancing the guide needle through the patient's tissue to a wound site;

removing the guide needle from within the introducer conduit, while leaving a distal end of the introducer conduit in the wound site;

threading a catheter, wherein the catheter comprises an elongated tube having a plurality of exit holes along the length thereof and a tubular porous membrane concentrically enclosed within said tube, through the introducer conduit;

removing the introducer conduit from the patient while leaving the infusion catheter in place in the wound site of the patient;

introducing fluid to the wound site through the infusion catheter; and wherein the pore diameter of the tubular porous membrane is approximately 0.45 micron.

* * * * *